(12) United States Patent
Suzuki

(10) Patent No.: US 10,983,671 B2
(45) Date of Patent: Apr. 20, 2021

(54) TERMINAL DEVICE, INFORMATION PROCESSING METHOD, AND INFORMATION PROCESSING PROGRAM

(71) Applicant: Rakuten, Inc., Tokyo (JP)

(72) Inventor: Fumie Suzuki, Tokyo (JP)

(73) Assignee: Rakuten, Inc., Tokyo (JP)

( * ) Notice: Subject to any disclaimer, the term of this patent is extended or adjusted under 35 U.S.C. 154(b) by 645 days.

(21) Appl. No.: 15/502,211

(22) PCT Filed: Sep. 7, 2015

(86) PCT No.: PCT/JP2015/075340
§ 371 (c)(1),
(2) Date: Feb. 7, 2017

(87) PCT Pub. No.: WO2017/042863
PCT Pub. Date: Mar. 16, 2017

(65) Prior Publication Data
US 2017/0235443 A1    Aug. 17, 2017

(51) Int. Cl.
*G06F 3/0482*    (2013.01)
*G06F 3/0484*    (2013.01)
(Continued)

(52) U.S. Cl.
CPC ........ *G06F 3/0482* (2013.01); *A61B 10/0012* (2013.01); *G06F 3/04847* (2013.01);
(Continued)

(58) Field of Classification Search
CPC ........ A61B 10/0012; A61B 2010/0019; G06F 3/0482; G06F 3/04847; G06F 19/00; G16H 10/20
See application file for complete search history.

(56) References Cited

U.S. PATENT DOCUMENTS

| 9,171,343 B1* | 10/2015 | Fischell | G16H 50/30 |
| 2007/0226626 A1* | 9/2007 | Yap | G06F 16/958 |
| | | | 715/733 |

(Continued)

FOREIGN PATENT DOCUMENTS

JP    2014-85682 A    5/2014

OTHER PUBLICATIONS

Author: Miyazaki, Title: Vital Information Input Acceptance System and Method, and Program, Publication Date : May 12, 2014, Assignee: Hitachi Systems LTD.*

(Continued)

*Primary Examiner* — Abdullah Al Kawsar
*Assistant Examiner* — David V Luu
(74) *Attorney, Agent, or Firm* — Sughrue Mion, PLLC

(57) ABSTRACT

An object is to prevent of display of display of candidates unlikely to be selected. An information processing device a target date associated with an input value to be input. The information processing device displays candidates for an input value on a screen. At this time, the information processing device displays a first number of candidates when the target date is included in a first period during which the information changes in a first range. The information processing device displays a second number of candidates that is smaller than the first number when the target date is included in a second period during which the information changes in a second range that is narrower than the first range. The first period and the second period is included in a cycle in which the information changes.

14 Claims, 15 Drawing Sheets

(51) Int. Cl.
    *G16H 10/20*       (2018.01)
    *A61B 10/00*       (2006.01)
    *G06F 19/00*       (2018.01)

(52) U.S. Cl.
    CPC ............. *G06F 19/00* (2013.01); *G16H 10/20* (2018.01); *A61B 2010/0019* (2013.01)

(56) References Cited

U.S. PATENT DOCUMENTS

| | | | | |
|---|---|---|---|---|
| 2013/0137940 | A1* | 5/2013 | Schafer | A61B 10/0012 600/301 |
| 2014/0123022 | A1* | 5/2014 | Lee | H04M 1/72566 715/747 |

OTHER PUBLICATIONS

Title: Understanding Ovulation—American Pregnancy Association. Publication Date: Jul. 6, 2015. URL: http://web.archive.org/web/20150706000222/https://americanpregnancy.org/getting-pregnant/understanding-ovulation/.*

* cited by examiner

FIG.3

MEMBER DB 12a

| USER ID |
| --- |
| PASSWORD |
| NAME |
| DATE OF BIRTH |
| GENDER |
| ZIP CODE |
| ADDRESS |
| TELEPHONE NUMBER |
| E-MAIL ADDRESS |
| ... |

BODY TEMPERATURE DB 12b

| USER ID |
| --- |
| MEASUREMENT DATE |
| BODY TEMPERATURE VALUE |

MENSTRUAL DATE DB 12c

| USER ID |
| --- |
| MENSTRUAL DATE |

ESTIMATION RESULT DB 12d

| USER ID |
| --- |
| MENSTRUAL DATE |
| ESTIMATED MENSTRUAL DATE |
| ESTIMATED NEXT MENSTRUAL DATE |

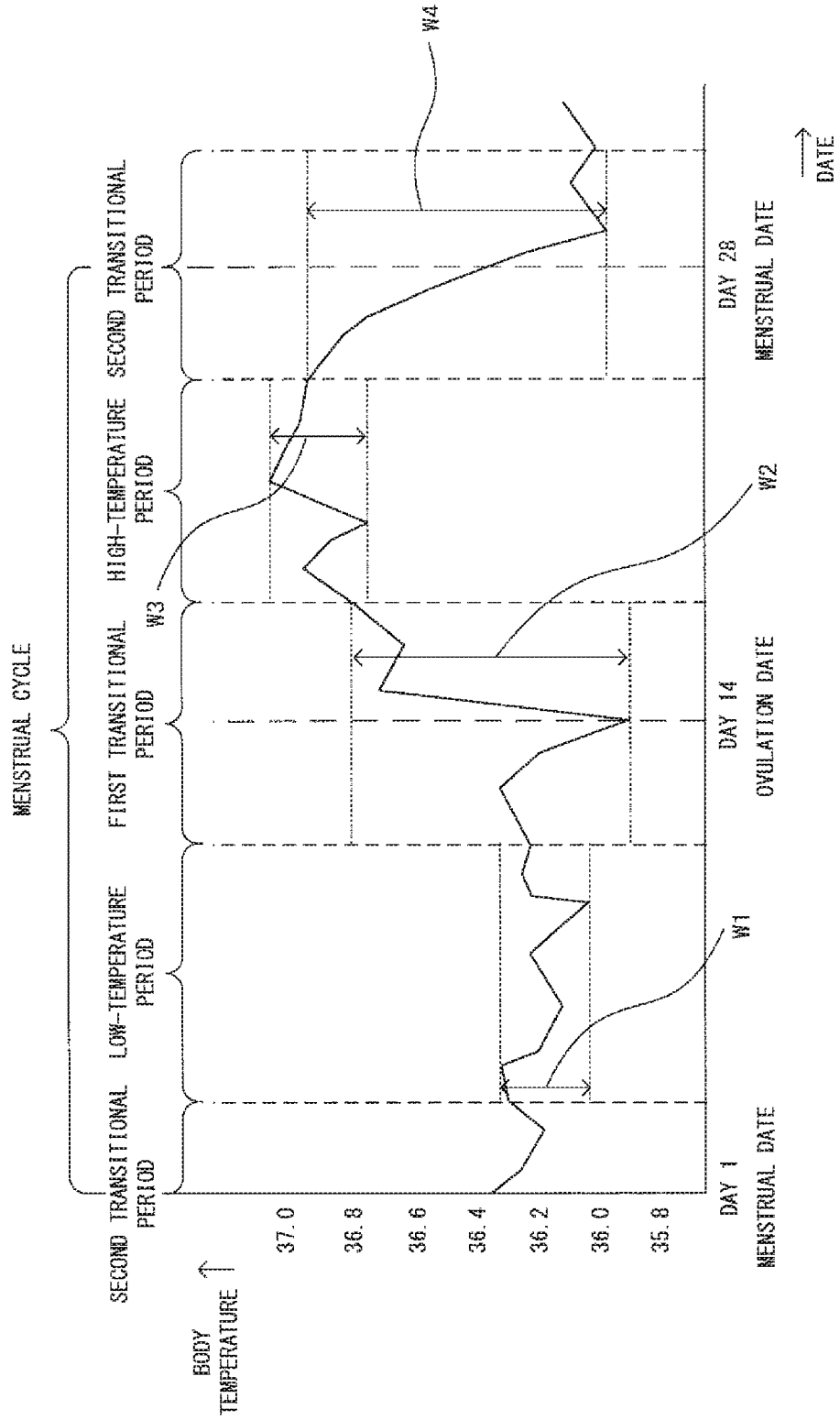

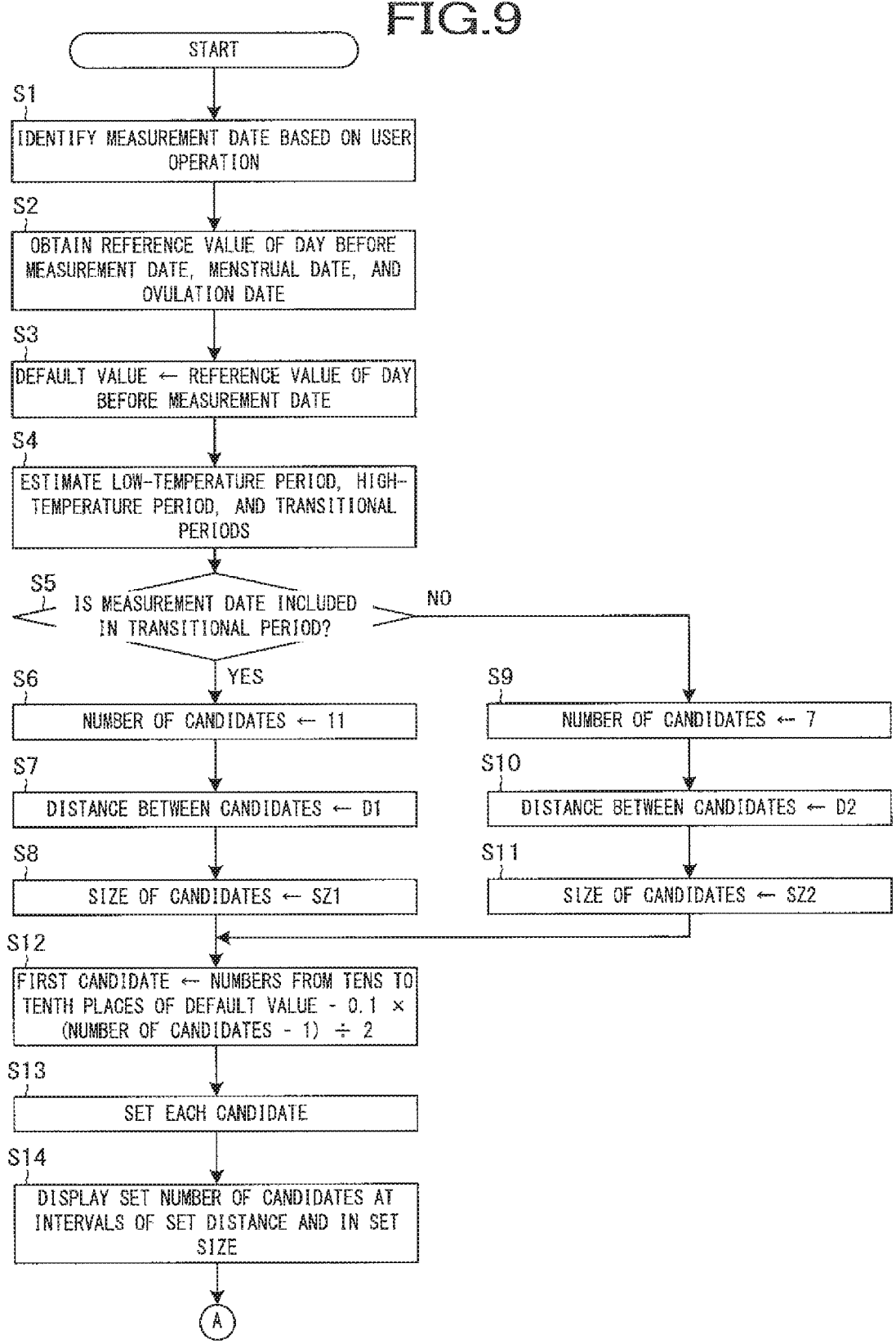

TERMINAL DEVICE, INFORMATION PROCESSING METHOD, AND INFORMATION PROCESSING PROGRAM

CROSS REFERENCE TO RELATED APPLICATIONS

This application is a National Stage of International Application No. PCT/JP2015/075340, filed on Sep. 7, 2015, the contents of all of which are incorporated herein by reference in their entirety.

TECHNICAL FIELD

The present invention relates to the technical field of terminal devices that assist in inputting numerical values of information that changes in a cyclic manner.

BACKGROUND ART

There is a known system that provides an interface for inputting numerical values of information that changes in a cyclic manner. An example of such information that changes in a cyclic manner is body temperature. For example, Patent Literature 1 discloses an information management server device that identifies candidate inputs of vital information based on the past inputs of vital information, and a mobile terminal that displays the candidate inputs on a display unit that in turn accepts an input of vital information selected from among the candidate inputs.

CITATION LIST

Patent Literature

Patent Literature 1: JP 2014-85682 A

SUMMARY OF INVENTION

Technical Problem

However, one cycle might include a period during which information rapidly changes and a period during which information slowly changes. In such a case, if the same number of candidates as that during the period with the rapid change are displayed during the period with the slow change, a large number of candidates unlikely to be actually selected by the user are displayed. The memory of the terminal device has to store candidate values for display and selection of candidates unlikely to be selected. As a large number of candidate values are stored, the space in the memory is wasted.

The present invention has been made in view of the above circumstances, and aims to provide a terminal device, an information processing method, and the like that enable preventing of display of candidates unlikely to be selected.

Solution to Problem

In order to achieve the above object, arm invention described in claim 1 is a terminal device comprising: an identifying means that identifies a target date associated with an input value to be input, the input value being an actual value of information at a point of time, the information changing in a cyclic manner; and a control means that displays candidates for the input value on a screen, the control means displaying a first number of candidates when the target date is included in a first period during which the information changes in a first range, the control means displaying a second number of candidates when the target date is included in a second period during which the information changes in a second range, the first period and the second period being included in a cycle in which the information changes, the second range being narrower than the first range, the second number being smaller than the first number.

According to this invention, in a case where the target date is included in the first period during which the information changes in a relatively wide range, the first number of candidates are displayed. In a case where the target date is included in the second period during which the information changes in a relatively narrow range, the second number, which is smaller than the first number, of candidates are displayed. Accordingly, during the second period with the narrower range of fluctuation of the information, display of candidates with low probabilities of being selected can be prevented. Thus, a smaller number of candidates than those during the first period are stored into the memory, and the space in the memory can be saved accordingly.

An invention described in claim 2 is the terminal device according to claim 1, wherein the control means displays the second number of candidates at longer intervals than intervals at which the first number of candidates are displayed.

According to this invention, in a case where the target date is included in the second period, a smaller number of candidates than those in a case where the target date is included in the first period are displayed. Accordingly, the second number of candidates can be displayed at longer intervals than the intervals at which the first number of candidates are displayed. Thus, the user can select a candidate as intended with higher precision.

An invention described in claim 3 is the terminal device according to claim 1 or 2, wherein the control means displays each of the second number of candidates in a larger size than a size of each of the first number of candidates.

According to this invention, in a case where the target date is included in the second period, a smaller number of candidates than those in a case where the target date is included in the first period are displayed. Accordingly, each of the second number of candidates can be displayed in a larger size than the size of each of the first number of candidates. Thus, the user can easily select a candidate as intended.

An invention described in claim 4 is the terminal device according to any one of claims 1 to 3, wherein the control means displays the candidates determined based on a reference value input as an actual value at a point of time on an earlier day than the target date.

According to this invention, the candidates to be displayed are determined based on the reference value that has been input as an actual value at a point of time on an earlier day than the target date. The difference between the reference value that has been input in the past and the actual value on the target date is probably smaller than the difference between a value that has not been input in the past and the actual value on the target date. Thus, the probability of the user selecting one of the candidates can be increased.

An invention described in claim 5 is the terminal device according to claim 4, wherein the control means displays the candidates including the reference value.

According to this invention, one of the displayed candidates is the reference value that has been input as the actual value at a point of time on an earlier day than the target date. The probability that the reference value that has been input in the past matches the actual value on the target date is higher than the probability that a value that has not been input in the past matches the actual value on the target date. Thus, the probability of the user selecting one of the candidates can be increased.

An invention described in claim 6 is the terminal device according to any one of claims 1 to 5, wherein: the second period includes a third period during which actual values of the information is relatively small, and a fourth period during which actual values of the information is relatively large; and the first period includes a fifth period during which a transition from the third period to the fourth period occurs, and a sixth period during which a transition from the fourth period to the third period occurs.

An invention described in claim 7 is the terminal device according to any one of claims 1 to 6, further comprising a determining means that determines at least one of the first number and the second number, the first number depending on the first range identified based on a history of inputs of actual values of the information, the second number depending on the second range identified based on the history, wherein the control means displays one of the determined first number and the determined second number of candidates.

According to this invention, the number of candidates to be displayed depends on the range of fluctuation of the information, the range being identified based on the history of inputs of actual values. Thus, an appropriate number of candidates for the user who inputs an input value can be displayed.

An invention described in claim 8 is the terminal device according to any one of claims 1 to 7, wherein: the information is body temperature; and the cycle in which the information changes is a menstrual cycle.

An invention described in claim 9 is the terminal device according to claim 8, wherein the control means estimates the first period to be a period with a predetermined length including one of an ovulation date and a menstrual date, and displays the second number of candidates when an amount of change in an actual value during a period from a predetermined number of days earlier than the day before the target date to the day before the target date is smaller than a predetermined amount in a case where the identified target date is included in the estimated first period.

According to this invention, even in a case where the target date is included in a period with a predetermined length including an ovulation date or a menstrual date, the second number of candidates are displayed if the amount of change in an actual value during the period from a predetermined number of days earlier than the day before the target date to the day before the target date is smaller than a predetermined amount. The period from a few days before an ovulation date or a menstrual date to the few days after the ovulation date or the menstrual date is normally the first period during which the actual value changes in a relatively wide range. However, if the amount of change in an actual value during the period from a predetermined number of days earlier than the day before the target date to the day before the target date is smaller than a predetermine (value, a transition from the first period to the second period has probably occurred before the target date. Through this estimation, an appropriate number of candidates can be displayed.

An invention described in claim 10 is an information processing method performed by a computer, the method comprising: an identifying step of identifying a target date associated with an input value to be input, the input value being an actual value of information at a point of time, the information changing in a cyclic manner; and a control step of displaying candidates for the input value on a screen, the control step comprising displaying a first number of candidates when the target date is included in a first period during which the information changes in a first range, and displaying a second number of candidates when the target date is included in a second period during which the information changes in a second range, the first period and the second period being included in a cycle in which the information changes, the second range being narrower than the first range, the second number being smaller than the first number.

An invention described in claim 11 is an information processing program for causing a computer to function as: an identifying means that identifies a target date associated with an input value to be input, the input value being an actual value of information at a point of time, the information changing in a cyclic manner; and a control means that displays candidates for the input value on a screen, the control means displaying a first number of candidates when the target date is included in a first period during which the information changes in a first range, the control means displaying a second number of candidates when the target date is included in a second period during which the information changes in a second range, the first period and the second period being included in a cycle in which the information changes, the second range being narrower than the first range, the second number being smaller than the first number.

Advantageous Effects of Invention

According to the invention, in a case where the target date is included in the first period during which the information changes in a relatively wide range, the first number of candidates are displayed. In a case where the target date is included in the second period during which the information changes in a narrower range, the second number, which is smaller than the first number, of candidates are displayed. Accordingly, during the second period with the narrower range of fluctuation of the information, display of candidates with low probabilities of being selected can be prevented. Thus, a smaller number of candidates than those during the first period are stored into the memory, and the space in the memory can be saved accordingly.

BRIEF DESCRIPTION OF DRAWINGS

FIG. 3 is a diagram showing an example of the contents registered in databases stored in a storage unit 12 of the information processing server 1.

FIG. 6 is a diagram showing an example of a body temperature graph.

FIG. 9 is a flowchart showing an example of a process to be performed by the system control unit 27 of a user terminal 2 according to an embodiment.

DESCRIPTION OF EMBODIMENTS

The following is a detailed description of embodiments of the present invention, with reference to the drawings. It should be noted that the embodiments described below are embodiments where the present invention is applied to an information processing system.

Figure 1:
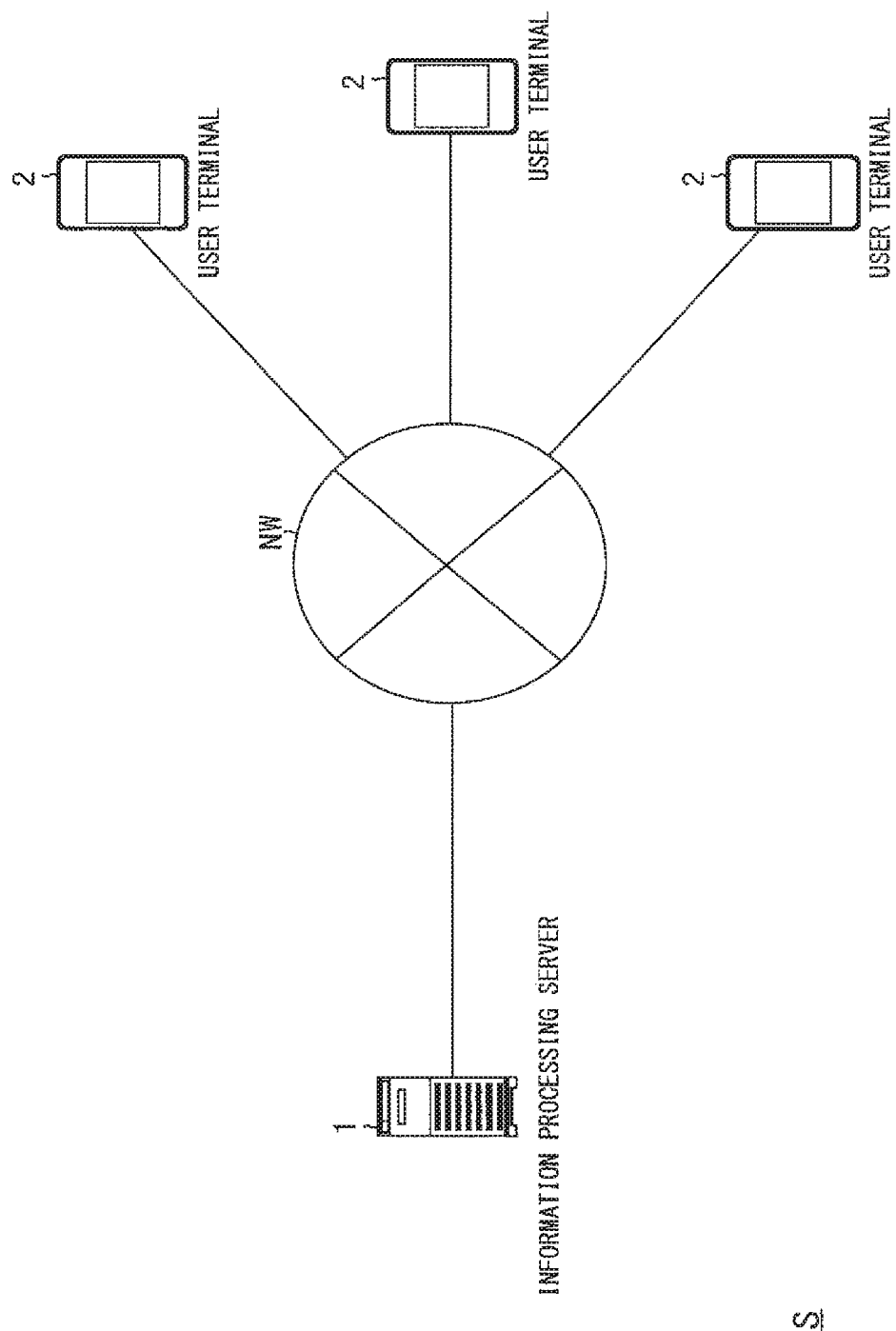
FIG. 1 is a diagram schematically showing an example configuration of an information processing system S according to one embodiment.

1. First Embodiment 1-1. Configuration of an Information Processing System and the Outline of the Functions Thereof Referring first to FIG. 1, the configuration of an information processing system S according to this embodiment and the outline of the functions thereof are described. FIG. 1 is a diagram schematically showing an example configuration of an information processing system S according to this embodiment.

As shown in FIG. 1, the information processing system S includes an information processing server 1 and user terminals 2. The information processing server 1 and each user terminal 2 can exchange data to each other via a network NO, using TAP/IP or the like as a communication protocol. The network NO is formed with the Internet, a special-purpose communications network (such as a community antenna television (CAT) network), or a mobile communications network (including base stations and the like), and a gateway or the like.

The information processing server 1 is a server device that distributes information related to women's health to the user terminals 2. The information processing server 1 also obtains information, such as the values of basal body temperatures, menstrual dates, and the like of users, from the user terminals 2. Based on the obtained information, the information processing server 1 estimates ovulation dates of the users, and predicts the next menstrual dates.

The user terminals 2 are terminal devices of the users who use the information processing system S. A user terminal 2 is an example of an information processing device according to the present invention. A user terminal 2 may be a smart phone, a tablet computer, a personal digital assistant (PDA), a personal computer, or the like. A user terminal 2 receives an input of a value of a user's basal body temperature measured with a thermometer, from the user. The value of the measured body temperature is also referred to as the "measured value". The measured value indicates an actual value of the body temperature at a certain point of time. The measured value is an example of an actual value according to the present invention. The value of the input body temperature is also referred to as the "inputs value". The user terminal 2 transmits the input body temperature value to the information processing server 1. The user terminal 2 also transmits an actual menstrual date input by the user, to the information processing server 1. The user terminal 2 then displays information, such as an ovulation date and a menstrual date estimated by the information processing server 1. It should be noted that the actual value may not be a measured numerical value of information. The actual value of information that changes with phenomena may be a value obtained by any appropriate method.

1-2. Configuration of the Information Processing Server

Figure 2:
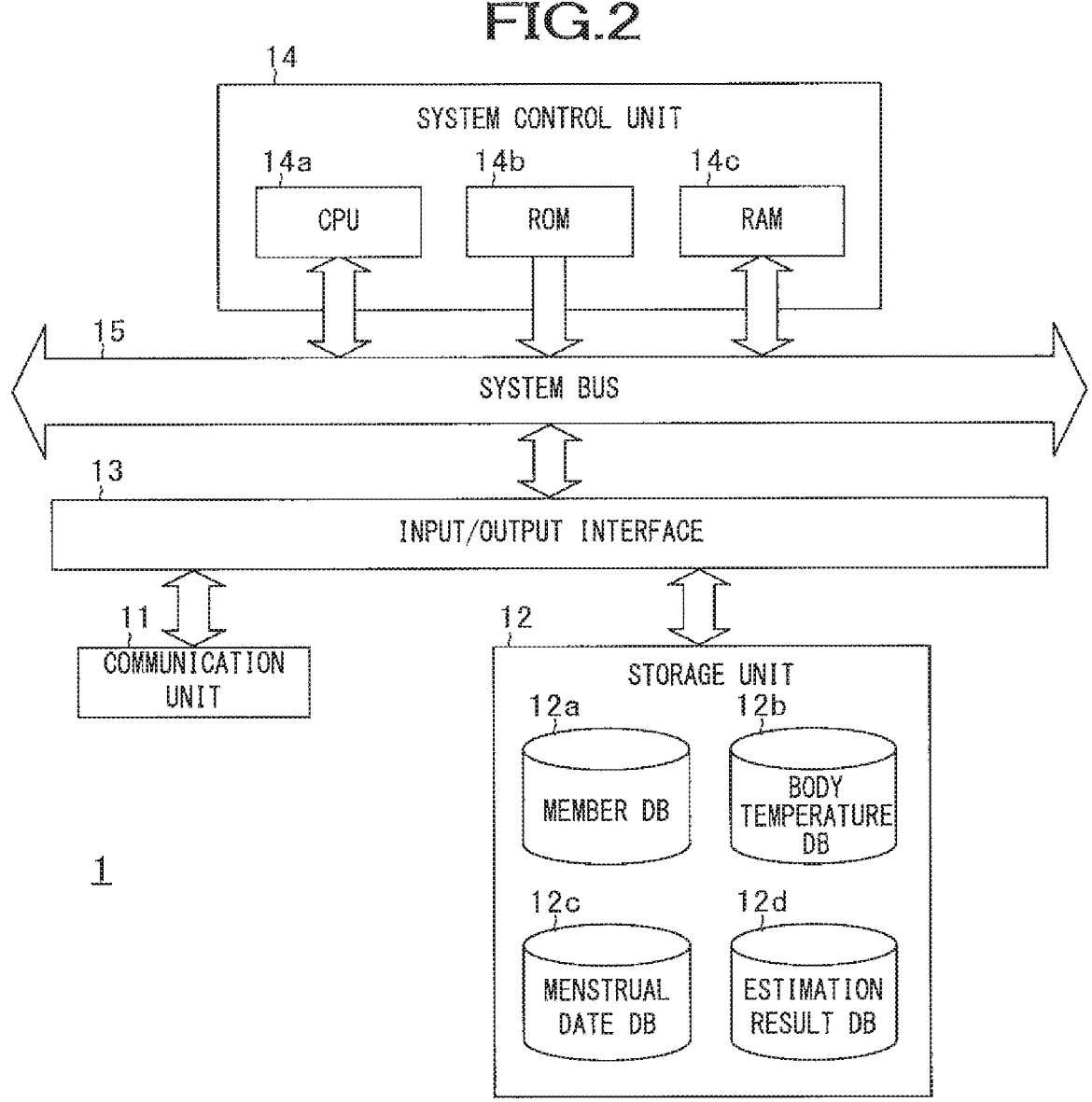
FIG. 2 is a block diagram schematically showing an example configuration of an information processing server 1 according to one embodiment.

Referring now to FIGS. 2 and 3, the configuration of the information processing server 1 is described.

FIG. 2 is a block diagram schematically showing an example configuration of the information processing server 1 according to this embodiment. As shown in FIG. 2, the information processing server 1 includes a communication unit 11, a storage unit 12, an input/output interface 13, and a system control unit 14. The system control unit 14 and the input/output interface 13 are connected to each other via a system bus 15.

The communication unit 11 is connected to the network NO, and controls the states of communication with the user terminals 2 and the like.

The storage unit 12 is formed with a hard disk drive, for example. This storage unit 12 stores databases, such as a member DB 12a, a body temperature DB 12b, a menstrual date DB 12c, and an estimation result DB 12d. "DB" stands for database. FIG. 3 is a diagram showing an example of the contents registered in the databases stored in the storage unit 12 of the information processing server 1.

The user information about the respective users who use the information processing system S is stored in the member DB 12a. Specifically, user attributes, such as an user ID, a password, names, a date of birth, a gender, a zip code, an address, a telephone number, and e-mail address, are associated with one another and are registered as user information in the member DB 12a. The user ID is the information for identifying a user.

Input values of basal body temperatures are registered in the body temperature DB 12b. Specifically, a user ID, a measurement date, and a body temperature value are associated with one another and are registered in the body temperature DB 12b. The user ID represents a user who has input a body temperature value. The measurement date indicates a date on which a body temperature has been measured. The body temperature value is an input value of a basal body temperature. For example, the system control unit 14 receives the user ID of the user who uses a user terminal 2, a measurement date, and a body temperature value from the user terminal 2. The system control unit 14 then registers the received information in the body temperature DB 12b.

Menstrual dates that have been input by users are registered in the menstrual date DB 12c. Specifically, a user ID and a measurement date are associated with each other and are registered in the menstrual date DB 12c. The user ID represents a user who has input a menstrual date. For example, the system control unit 14 receives the user ID of the user who uses a user terminal 2 and the menstrual date input by the user, from the user terminal 2. The system control unit 14 then registers the received information in the menstrual date DB 12c.

Estimated ovulation dates and menstrual dates are registered in the estimation result DB 12d. Specifically, a user ID, a menstrual date input by a user, an estimated ovulation date, and an estimated next menstrual date are associated with one another and are registered in the estimation result DB 12d. The user ID represents the user whose ovulation date and menstrual date are estimated. The estimated ovulation date is a date estimated as the ovulation date in the menstrual cycle having the menstrual date input by the user as its first day. The estimated next menstrual date is a date estimated as the next menstrual date after the menstrual date input by the user.

The storage unit 12 stores various kinds of programs, such as an operating system, a World Wide Web (WOW) server program, a database management system (DAMS), and a prediction process program. The prediction process program is a program for estimating an ovulation date and predicting a menstrual date.

The input/output interface 13 is designed to perform interfacing between the communication unit 11 and the storage unit 12, and the system control unit 14.

The system control unit 14 includes a CPU 14a, a read only memory (ROM) 14b, and a random access memory (RAM) 14c. The system control unit 14 estimates an ovulation date and predicts a menstrual date, based on the body temperature DB 12b and/or the menstrual date DB 12c. The system control unit 14 associates the estimated ovulation date and menstrual date as the estimated ovulation date and the estimated next menstrual date with the user ID and the menstrual date of the target user, and then registers the estimated dates in the estimation result DB 12d. As for the ovulation date estimation method and the menstrual date prediction method, the system control unit 14 may use any method that uses body temperatures measured in the past and/or menstrual dates in the past. The system control unit 14 may estimate an ovulation date and a menstrual date when a new body temperature value is input by a user, for example. Alternatively, the system control unit 14 may estimate an ovulation date and a menstrual date when a new menstrual date is input by a user, for example.

The system control unit 14 may predict the next menstrual date based on a user's past menstrual dates stored in the menstrual date DB 12c, for example. For example, the period from a menstrual date to the day before the next menstrual date is a menstrual cycle. The system control unit 14 may predict the number of days in the current menstrual cycle from the representative value of the past menstrual cycles, for example. The representative value may be the mean value, the median value, or the mode value, for example. The system control unit 14 may predict a menstrual date as the date that is the number of days in the estimated current menstrual cycle after the first day of the current menstrual cycle or the latest menstrual date. Also, the system control unit 14 may estimate an ovulation date that is a predetermined number of days before a predicted menstrual date. The predetermined number of days may be 14 days, for example. On an ovulation date, an egg is released from a follicle. As a result, a corpus lutetium is formed from the follicle. Presentational hormone is secreted from this corpus lutetium. Due to this presentational hormone, the body temperature rises, and a transition from a low-temperature period to a high-temperature period occurs. As the corpus lutetium regresses, the secretion of the presentational hormone ends. As a result, the lining of the uterus is shed, and a menstrual period begins. Also, as the secretion of the presentational hormone ends, the body temperature drops. Therefore, a transition to the low-temperature period of the next menstrual cycle occurs. The life-span of the presentational hormone is considerably stable. For example, the life-span of the corpus lutetium is normally 14 days with a margin of error of ±2 days. It should be noted that, instead of the information processing server 1, a user terminal 2 may estimate an ovulation date and a menstrual date of the user who uses the user terminal 2.

1-3. Configuration of a User Terminal

Figure 4:
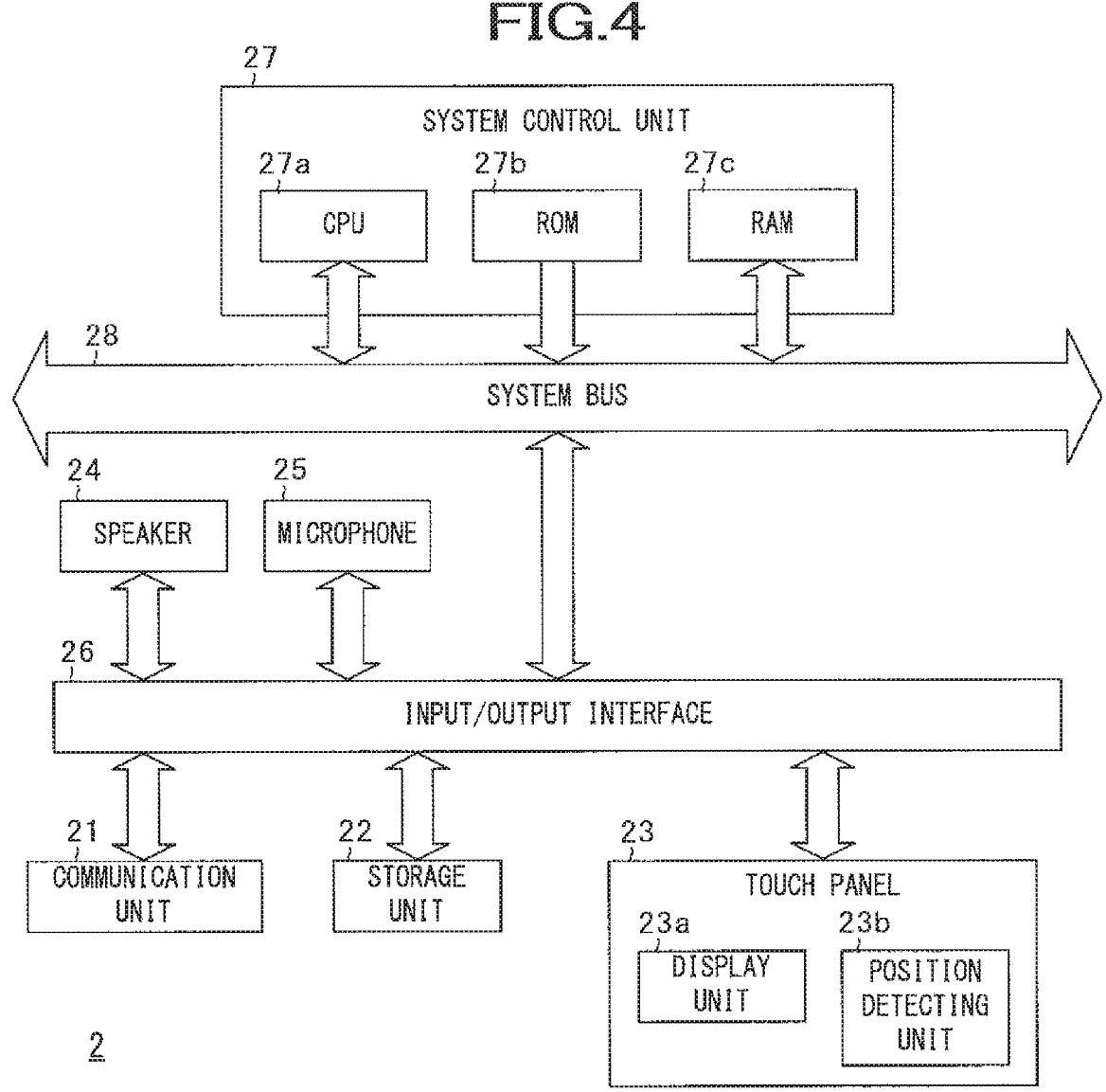
FIG. 4 is a block diagram schematically showing an example configuration of a user terminal 2 according to one embodiment.

Referring now to FIG. 4, the configuration of a user terminal 2 is described.

FIG. 4 is a block diagram schematically showing an example configuration of a user terminal 2 according to this embodiment.

As shown in FIG. 4, a user terminal 2 includes a communication unit 21, a storage unit 22, a touch panel 23, a speaker 24, a microphone 25, an input/output interface 26, and a system control unit 27. The system control unit 27 and the input/output interface 26 are connected to each other via a system bus 28.

The communication unit 21 is connected to the network NO, and controls the state of communication with the information processing server 1 and the like.

The storage unit 22 is formed with a flash memory, for example. The storage unit 22 stores an operating system and a terminal application program. The terminal application program is an example of an information processing program according to the present invention. The terminal application program is a program for accepting inputs of a body temperature value and a menstrual date, and displaying an estimated ovulation date and a predicted menstrual date. The terminal application program may be downloaded from the information processing server 1 via the network NO, for example. Alternatively, the terminal application program may be recorded on a recording medium, such as an optical disk, a magnetic tape, or a memory card, and be loaded via a drive device. Also, the terminal application program may be a program product.

The touch panel 23 functions as a display and an input device. The touch panel 23 includes a display unit 23a and a position detecting unit 23b. The display unit 23a is formed with a liquid crystal display, for example, and is designed to display information, such as text and an image. The display unit 23a is an example of a display means according to the present invention. The position detecting unit 23b detects the coordinates of a point at which a user touches the touch panel 23 with a finger, a "touch pen" (a stylus pen), or the like. The position detecting unit 23b then outputs the detected coordinates to the system control unit 27. It should be noted that the user terminal 2 may include a display and a pointing device, for example, instead of the touch panel 23. By operating the pointing device, the user can designate desired coordinates on the screen of the display. The pointing device may be a mouse or a touch-pad, for example.

The input/output interface 26 is designed to perform interfacing between the components from the communication unit 21 to the microphone 25, and the system control unit 27.

The system control unit 27 includes a CPU 27a, a ROM 27b, and a RAM 27c.

1-4. Outline of the Functions of the System Control Unit of a User Terminal

Figure 5:
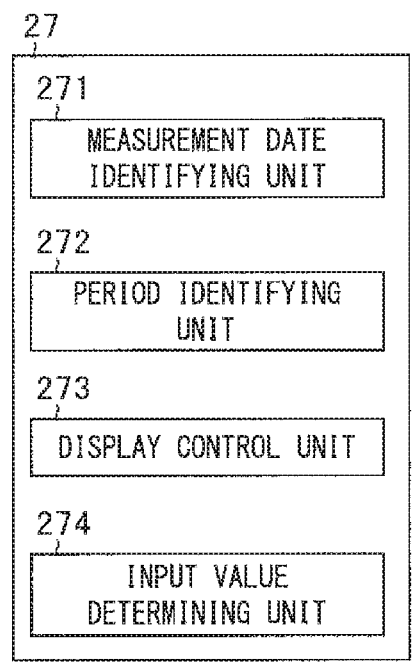
FIG. 5 is a diagram showing an example of the functional block of the system control unit 27 of a user terminal 2 according to one embodiment.

Referring now to FIGS. 5 to 8B, the outline of the functions of the system control unit 27 is described. FIG. 5 is a diagram showing an example of the functional block of the system control unit 27 of a user terminal 2 according to this embodiment. As the CPU 27a reads and executes the terminal application program, the system control unit 27 functions as a measurement date identifying unit 271, a period identifying unit 272, a display control unit. 273, an input value determining unit 274, and the like, as shown in FIG. 5. The measurement date identifying unit 271 is an example of an identifying means according to the present invention. The period identifying unit 272 and the display control unit 273 are an example of a control means and a determining means according to the present invention.

By executing the terminal application program, the system control unit 27 accepts an input of the value of a body temperature actually measured, from a user. Specifically, the system control unit 27 displays candidates for the input body temperature or the input value. The system control unit 27 determines the input value to be a candidate selected by the user from among the candidates. In doing so, the system control unit 27 prevents display of the candidates with low probabilities of being selected, as will be described later in detail.

The measurement date identifying unit 271 identifies the measurement date associated with the current input value of the body temperature. The measurement date associated with the input value is the date on which the body temperature indicated by the input value was measured. For example, if the user has not designated any measurement date, the measurement date identifying unit 271 may identify today's date as the measurement date, based on the user's operation on the touch panel 23. If the user has designated a measurement date, the measurement date identifying unit 271 identifies the designated measurement date. The user can input the value of a body temperature measured in the past. The measurement date identifying unit 271 may function not to allow designation of a measurement date. In that case, the measurement date identifying unit 271 may invariably identify today's date as the measurement date.

The period identifying unit 272 determines which one of the stable body temperature periods and the transitional periods in a menstrual cycle includes the measurement date identified by the measurement date identifying unit 271. FIG. 6 is a diagram showing an example of a body temperature graph. The body temperature of a woman changes in a cyclic manner. The period from a menstrual date to the next menstrual date forms one menstrual cycle. One menstrual cycle includes stable body temperature periods and transitional periods. The stable body temperature periods are an example of a second period according to the present invention. The transitional periods are an example of a first period according to the present invention. During the stable body temperature periods, the body temperature is relatively stable in the menstrual cycle. The stable body temperature periods include a low-temperature period and a high-temperature period. During the low-temperature period, the body temperature is relatively low in the menstrual cycle. The body temperature during the low-temperature period is relatively stable. During the high-temperature period, the body temperature is relatively high in the menstrual cycle. The body temperature during the high-temperature period is relatively stable. The difference between the mean of body temperatures during the low-temperature period and the mean of body temperatures during the high-temperature period is approximately 0.3 to 0.5 degrees, for example. During the transitional periods, the body temperature changes by relatively large amounts in the menstrual cycle, and the body temperature is unstable. The transitional periods include a first transitional period and a second transitional period. During the first transitional period, a transition from the low-temperature period to the high-temperature period occurs. The first transitional period includes the ovulation date. During the second transitional period, a transition from the high-temperature period to the low-temperature period occurs. The second transitional period includes the menstrual date. That is, during the second transitional period, the menstrual cycle enters the next menstrual cycle. The low-temperature period is an example of a third period according to the present invention. The high-temperature period is an example of a fourth period according to the present invention. The first transitional period is an example of a fifth period according to the present invention. The second transitional period is an example of a sixth period according to the present invention.

During the stable body temperature periods, the body temperature fluctuates less widely than the body temperature during the transitional periods. A range of fluctuation of the body temperature may be the difference between the smallest value and the largest value of body temperatures during a period, for example. In FIG. 6, We indicates the range of fluctuation of the body temperature during the low-temperature period, We indicates the range of fluctuation of the body temperature during the first transitional period, We indicates the range of fluctuation of the body temperature during the high-temperature period, and We indicates the range of fluctuation of the body temperature during the second transitional period. Both the fluctuation ranges We and We are smaller than the fluctuation ranges We and We.

The period identifying unit 272 may identify the stable body temperature periods and the transitional periods, for example. From the information processing server 1, the period identifying unit 272 may obtain the menstrual dates in the past, and the ovulation date and the next menstrual date estimated by the information processing server 1, for example. The period identifying unit 272 may estimate the first transitional period that starts a set number of days before the ovulation date and ends the set number of days after the ovulation date, and estimate the second transitional period that starts the set number of days before the menstrual date and ends the set number of days after the menstrual date. The period identifying unit 272 may estimate the low-temperature period that starts on the day after the second transitional period and ends on the day before the first transitional period, and estimate the high-temperature period that starts on the day after the first transitional period and ends the day before the second transitional period. The set number of days that determines the number of days in each transitional period may be set in advance, for example. The set number of days may be three, for example. Also, the period identifying unit 272 may determine the set number of days based on the number of days in the menstrual period of the user who inputs the body temperature and/or the fluctuations of the body temperature in the past, for example. The period identifying unit 272 determines which one of the estimated stable body temperature periods and transitional periods includes the measurement date.

The display control unit 273 causes candidates for the input value to be displayed as choices on a screen. First, the display control unit 273 determines the number of candidates for the input value to be displayed on the display unit 23a. Specifically, if the measurement date is included in a transitional period, the display control unit 273 determines a first number to be the number of candidates. If the measurement date is included in a stable body temperature period, on the other hand, the display control unit 273 determines a second number to be the number of candidates. The second number is smaller than the first number. That is, if the measurement date is included in a transitional period, the display control unit 273 displays the first number of candidates. If the measurement date is included in a stable body temperature period, the display control unit 273 displays the second number of candidates. The body temperature during a transitional period is less stable than that during a stable body temperature period. To increase the probability of the user selecting one of the candidates displayed on one screen, a large number of candidates should be displayed on one screen. However, only one candidate is actually selected as an input value by the user from among the candidates. In a case where the measurement date is included in a stable body temperature period, the range of fluctuation of the body temperature is narrower than that in a case where the measurement date is included in a transitional period. If the same number of candidates as that in a case where the measurement date is included in a transitional period are displayed in a case where the measurement date is included in a stable body temperature period, many displayed candidates are not actually selected by the user. In this case, the user terminal 2 needs to store, into the RAM 27c, information for display and selection of candidates unlikely to be selected by the user. To counter this, the display control unit 273 reduces the number of candidates to be displayed in a case where the measurement date is included in a stable body temperature period, to a smaller number than the number of candidates to be displayed in a case where the measurement date is included in a transitional period. In this manner, the amount of information to be stored in the RAM 27c can be reduced. Also, as a smaller number of candidates than that in a case where the measurement date is included in a transitional period are displayed in one screen, each candidate can be displayed in a larger size. Further, the distance between candidates can be made longer. Accordingly, it becomes easier for the user to select a candidate by designating coordinates on a screen, using the touch panel 23 or a pointing device.

The first number and the second number may be set in advance, for example. In a case where the difference between adjacent candidate body temperatures is 0.1, for example, the first number may be 11, and the second number may be five. The first number and the second number may be set in advance, based on the statistics on the ranges of fluctuation of the body temperatures during the transitional periods and the stable body temperature periods of all the users, and the differences between adjacent candidate body temperatures. For example, representative values of the respective ranges of fluctuation of the body temperatures during the transitional periods and the stable body temperature periods may be calculated. A representative value may be a mean value, a median value, a predetermined percentile, or a mode value, for example. Also, the number of candidates may be calculated as follows, for example: the representative value of the ranges of fluctuation÷0.1×2+1. As the first number and the second number are appropriately set, the smallest possible number of candidates can be displayed both during a transitional period and during a stable body temperature period. The smallest possible number of candidates are such a number of candidates as to increase the probability of the user selecting one of displayed candidates while minimizing the space in the RAM 27c for storing the information for display and selection of candidates. In a case where the displayed candidates do not include a body temperature value to be input by the user, the user needs to perform an operation so that the body temperature value can be displayed as a candidate. The user can be free from performing such a complicated operation.

The display control unit 273 determines a value of each candidate. For example, the display control unit 273 may determine the value of each candidate so that the difference in value between adjacent candidates becomes a predetermined difference. The display control unit 273 may determine the values of candidates based on a value that has been input as a measured value at a point of time on a day that is earlier than the measurement date associated with the current input value. The value to be used in determining candidates is called the "reference value". The body temperature changes in a cyclic manner. Therefore, the difference between the reference value that has been input in the past and the body temperature value on the measurement date is probably smaller than the difference between a body temperature value that has not been input in the past and the body temperature value on the measurement date. Thus, the probability of the user selecting one of the candidates can be increased. For example, the display control unit 273 may determine reference values to be the respective body temperature values that have been input during a predetermined period that is earlier than the measurement date. The display control unit 273 may then calculate a representative value of the reference values. The representative value may be the mean value, the median value, or the mode value, for example. The display control unit 273 may determine candidates that include the calculated representative value. The display control unit 273 may determine the calculated representative value to be any of the candidates. The display control unit 273 may determine the representative value to be the median value of the candidates, or to be one of the candidates other than the median value. Also, the display control unit 273 may determine the reference value to be a value that has been input as a measured value at a point of time on a day that is earlier than the measurement date associated with the current input value. The display control unit 273 may then determine candidates including the reference value. The probability that the reference value that has been input in the past matches the body temperature value on the measurement date is higher than the probability that a body temperature value that has not been input in the past matches the body temperature value on the measurement date. Thus, the probability of the user selecting one of the candidates can be increased. For example, the display control unit 273 may determine the reference value to be a value that has been input as a measured value at a point of time on the day before the current measurement date. The display control unit 273 may determine the reference value to be the median value of the candidates, or to be one of the candidates other than the median value. After determining the value of one candidate, the display control unit 273 may determine the value of another candidate based on the determined value of the candidate.

The display control unit 273 may determine one of the candidates to be the default value of an input value. The display control unit 273 may determine the reference value or the representative value of reference values to be the default value, or may determine some other candidate to be the default value. Also, the display control unit 273 may determine the default value to be the median value of the candidates.

Figure 7A:
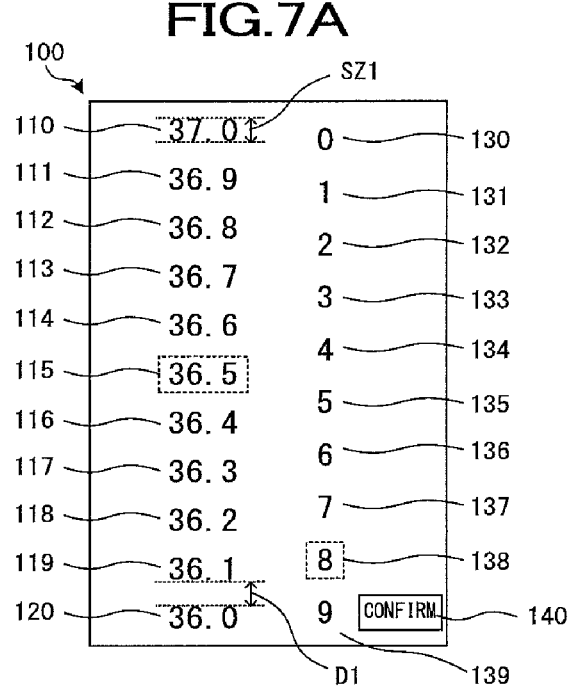
FIG. 7A is a diagram showing an example of display of candidates for the input value in a case where the target date is included in a transitional period.

FIG. 7A is a diagram showing an example of display of candidates for the input value in a case where the measurement date is included in a transitional period. The screen of the display unit 23a includes a display area 100. The display area 100 is an area for displaying candidates for the input value. A part of the screen may be the display area 100, or the entire screen may be the display area 100. In a case where the measurement date is included in a transitional period, candidates 110 to 120, candidate fractional parts 130 to 139, and a confirmation button 140 are displayed in the display area 100. The default value is 36.58 degrees, for example. The default value is divided into "36.5", which is indicated by the respective numbers in the tens place, the ones place, and the tenth place, and "8", which is indicated by the number in the hundredth place. In this embodiment, the value ("36.5", for example) indicated by a part of the number representing the default value is an example of a median value according to the present invention. In other embodiments, the default value may also be the median value.

The candidates 110 to 120 are candidates for the input value that are indicated by the numbers in the tens place, the ones place, and the tenth place. The candidate 110 is "37.0", the candidate 111 is "36.9", the candidate 112 is "36.8", the candidate 113 is "36.7", the candidate 114 is "36.6", the candidate 115 is "36.5", the candidate 116 is "36.4", the candidate 117 is "36.3", the candidate 118 is "36.2", the candidate 119 is "36.1", and the candidate 120 is "36.0". That is, eleven candidates are displayed. The respective values of the candidates 110 to 120 change depend on the default value. In the example shown in FIG. 7A, the candidates are arranged in the vertical direction. However, the candidates may be arranged in the horizontal direction. A mark indicating that the candidate 115 is currently selected is displayed on the candidate 115. However, this mark may not be displayed. The distance between adjacent candidates among the candidates 110 to 120 is D1. The size of each of the candidates 110 to 120 is SZ1.

The display control unit 273 may change the values of the candidates displayed in the display area 100, based on a user operation, for example. For example, new candidates may be displayed when the user scrolls the candidates 110 to 120 up or down. In this manner, the user can select a body temperature value even in a case where the actual body temperature value is not included in the candidates 110 to 120.

The candidate fractional parts 130 to 139 are candidates for the input value indicated by the number in the hundredth place. The candidate fractional part 130 is "0", the candidate fractional part 131 is "1", the candidate fractional part 132 is "2", the candidate fractional part 133 is "3", the candidate fractional part 134 is "4", the candidate fractional part 135 is "5", the candidate fractional part 136 is "6", the candidate fractional part 137 is "7", the candidate fractional part 138 is "8", and the candidate fractional part 139 is "9". The number of the candidate fractional parts remains the same in a stable body temperature period. Also, even if the default value changes, the respective values of the candidate fractional parts 130 to 139 do not change. A mark indicating that the candidate fractional part 138 is currently selected is displayed on the candidate fractional part 138.

The confirmation button 140 is the key for confirming that a selected candidate is an input value. However, the confirmation button 140 may not be displayed. For example, an input value may be confirmed after the user selects a candidate from among the candidates 110 to 120, and selects a candidate fractional part from among the candidate fractional parts 130 to 139.

Figure 7B:
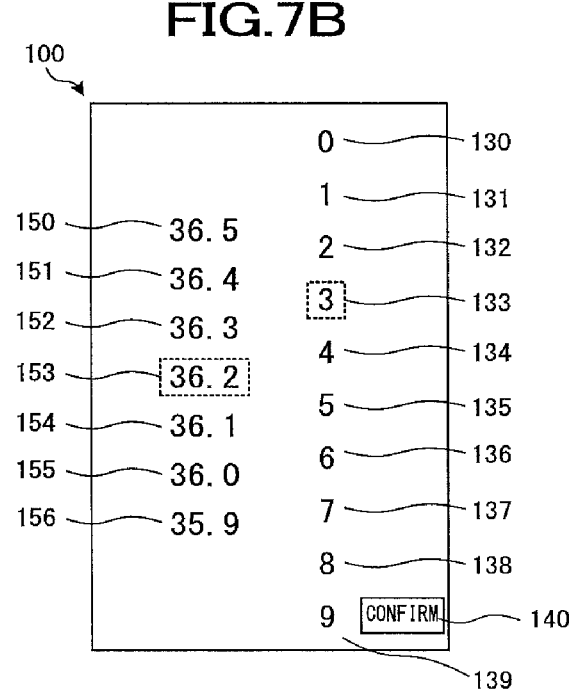
FIG. 7B is a diagram showing an example of display of candidates for the input value in a case where the target date is included in a stable body temperature period.

FIG. 7B is a diagram showing an example of display of candidates for the input value in a case where the measurement date is included in a stable body temperature period. In a case where the measurement date is included in a stable body temperature period, candidates 150 to 156, the candidate fractional parts 130 to 139, and the confirmation button 140 are displayed in the display area 100. The default value is 36.23 degrees, for example. The candidates 150 to 156 are candidates for the input value indicated by the numbers in the tens place, the ones place, and the tenth place. The candidate 150 is "36.5", the candidate 151 is "36.4", the candidate 152 is "36.3", the candidate 153 is "36.2", the candidate 154 is "36.1", the candidate 155 is "36.0", and the candidate 156 is "35.9". That is, seven candidates are displayed. In FIG. 7B, the distance between adjacent candidates among the candidates 150 to 156, and the size of each of the candidates 150 to 156 are the same as those in the case of FIG. 7A. A mark indicating that the candidate 153 is currently selected is displayed on the candidate 153.

Figure 8A:
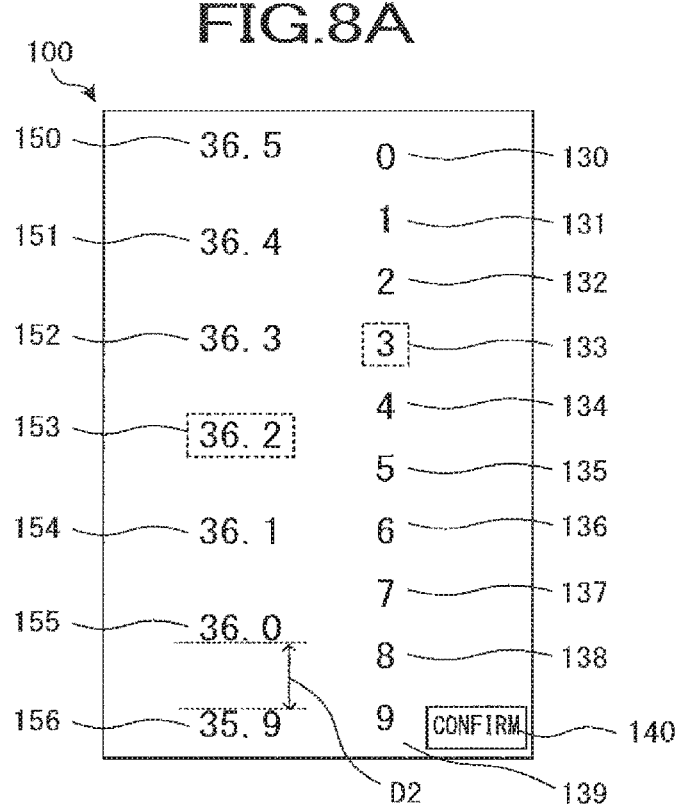
FIG. 8A is a diagram showing an example of display of candidates for the input value in a case where the target date is included in a stable body temperature period.

In a case where the measurement date is included in a stable body temperature period, the display control unit 273 may display the candidates at longer intervals than the intervals at which the candidates are displayed in a case where the measurement date is included in a transitional period, for example. This enables the user to select a candidate as intended with higher precision. As a result, the user can easily select a candidate. FIG. 8A is a diagram showing an example of display of candidates for the input value in a case where the measurement date is included in a stable body temperature period. FIG. 8A differs from FIG. 7B in that the distance between adjacent candidates among the candidates 150 to 156 is longer than that in the case of FIG. 7B. That is, in FIG. 8A, the distance between adjacent candidates among the candidates 150 to 156 is longer than the distance between adjacent candidates among the candidates 110 to 120 shown in FIG. 7A. The distance between adjacent candidates among the candidates 150 to 156 is Dr.

Figure 8B:
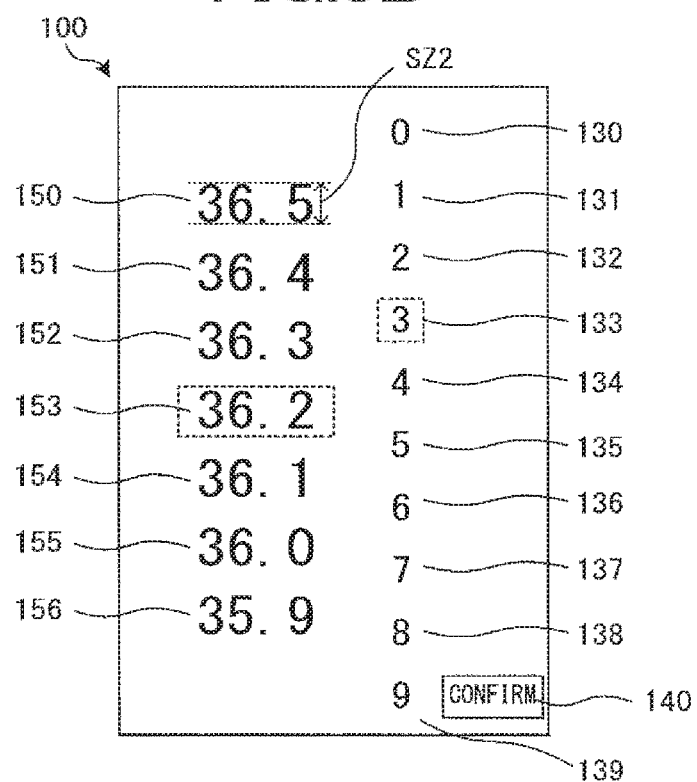
FIG. 8B is a diagram showing an example of display of candidates for the input value in a case where the target date is included in a stable body temperature period.

In a case where the measurement date is included in a stable body temperature period, the display control unit 273 may display the candidates in a larger size than the size of the candidates that are displayed in a case where the measurement date is included in a transitional period, for example. This facilitates the user to select a candidate as intended. FIG. 8B is a diagram showing an example of display of candidates for the input value in a case where the measurement date is included in a stable body temperature period. FIG. 8B differs from FIG. 7B in that the display size of the candidates 150 to 156 is larger than that in the case of FIG. 7B. That is, in. FIG. 8B, the display size of each of the candidates 150 to 156 is larger than the display size of each of the candidates 110 to 120 shown in FIG. 7A. The size of each of the candidates 150 to 156 is SZ2.

In a case where the measurement date is included in a stable body temperature period, the display control unit 273 may display candidates at longer intervals than the intervals at which the candidates are displayed in a case where the measurement date is included in a transitional period, for example. Also, in a case where the measurement date is included in a stable body temperature period, the display control unit 273 may display the candidates in a larger size than the size of the candidates that are displayed in a case where the measurement date is included in a transitional period.

The input value determining unit 274 determines an input value based on an operation performed by the user on the touch panel 23. For example, the input value determining unit 274 sets a selected value as the default value. The selected value is the body temperature value currently selected by the user. The candidate located in a position designated by the user from among the candidates 110 to 120 or the candidates 150 to 156 on the screen is determined to be a new selected value indicated by the numbers in the tens place, the ones place, and the tenth place. The input value determining unit 274 also determines that the candidate located in a position designated by the user from among the candidate fractional parts 130 to 139 on the screen is a new selected value indicated by the number in the hundredth place. In a case where the user selects the confirmation button 140, the input value determining unit 274 determines the current selected value to be the input value.

It should be noted that the system control unit 14 of the information processing server 1 may function as the measurement date identifying unit 271, the period identifying unit 272, and the display control unit 273. In that case, the system control unit 27 of each user terminal 2 may function only as the input value determining unit 274. For example, the system control unit 14 of the information processing server 1 receives a measurement date designated by a user from the user terminal 2. The system control unit 14 also determines which one of the stable body temperature periods and the transitional periods includes the measurement date, based on the menstrual date DB 12c and the estimation result DB 12d. The system control unit 14 also transmits candidates for the input value to the user terminal 2. The candidates for the input value are determined based on the default value and which of the stable body temperature periods and the transitional periods includes the measurement date. By doing so, the system control unit 14 causes the user terminal 2 to display the candidates for the input value on the display unit 23a. In this case, the user terminal 2 needs to store only the candidates for the input value into the RAM 27c or the storage unit 22. The user terminal 2 does not need to store the body temperature values, the ovulation dates, and the menstrual dates of the user into the RAM 27c or the like.

1-5. Operation of the Information Processing System

Figure 10:
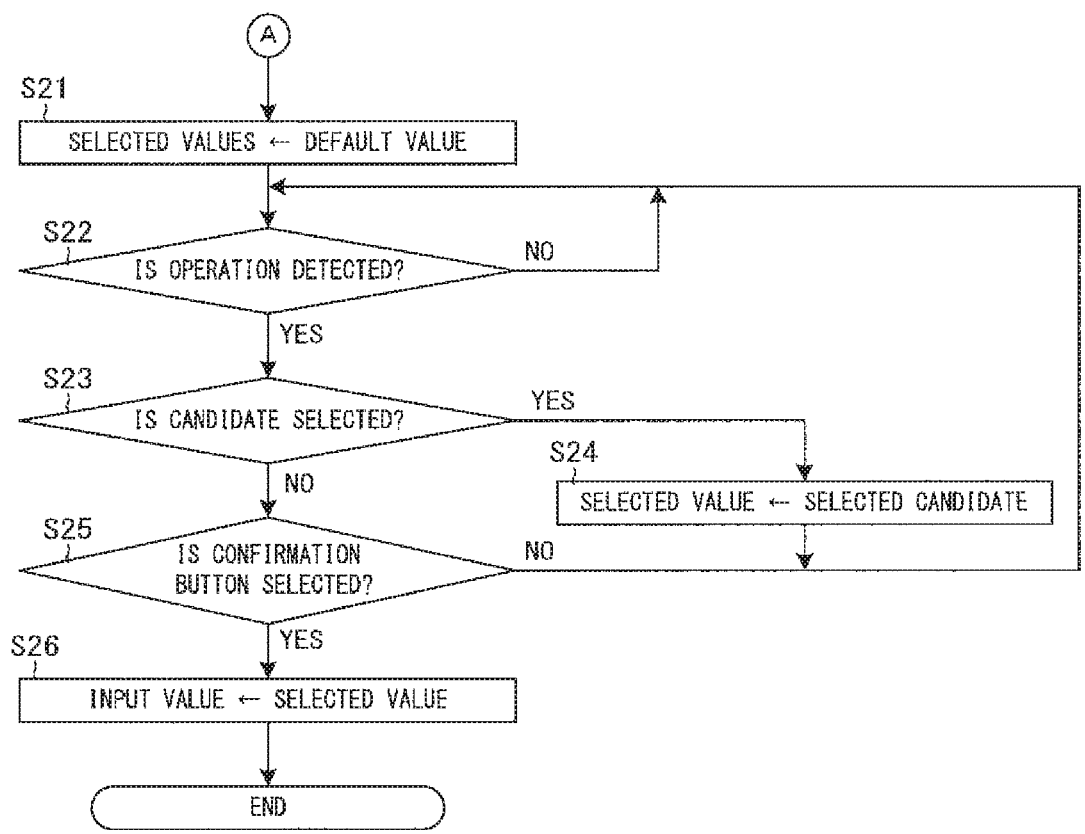
FIG. 10 is a flowchart showing an example of a process to be performed by the system control unit 27 of a user terminal 2 according to an embodiment.

Referring now to FIGS. 9 and 10, operation of the information processing system S is described. In the case described below, a body temperature value on the day before the measurement date is obtained as the reference value, and the reference value is determined to be the default value and the median value of candidates. FIGS. 9 and 10 are flowcharts showing an example of a process to be performed by the system control unit 27 of a user terminal 2 according to this embodiment. The user operates the touch panel 23, to activate the terminal application program. As the user selects a body temperature value input from the menu in the terminal application program, the system control unit 27 performs the process shown in FIG. 9.

As shown in FIG. 9, the measurement date identifying unit 271 identifies the measurement date, based on an operation performed by the user on the touch panel 23 (step S1). For example, the measurement date identifying unit 271 displays a menu on the screen of the display unit 23a for the user. In a case where the user selects "inputting today's body temperature" from the menu, the measurement date identifying unit 271 identifies today's date as the measurement date. In a case where the user selects "designating a date" from the menu, on the other hand, the measurement date identifying unit 271 identifies the date input by the user as the measurement date.

Next, the measurement date identifying unit 271 obtains the reference value from the information processing server 1. The reference value is the body temperature value on the day before the measurement date among the past body temperature values of the user using the user terminal 2. The measurement date identifying unit 271 also obtains a menstrual date and an ovulation date of the user using the user terminal 2, from the information processing server 1 (step S2). For example, the measurement date identifying unit 271 transmits an information request to the information processing server 1. The information request includes the user ID of the user using the user terminal 2, the measurement date, and the date of the day before the measurement date. The information processing server 1 obtains, from the body temperature DB 12b, the body temperature value associated with the day before the measurement date among the body temperature values associated with the user ID included in the information request. The information processing server 1 also obtains, from the menstrual date DB 12c, the menstrual date within a predetermined period of time before the measurement date among the menstrual dates associated with the user ID included in the information request. The predetermined period of time may be a few weeks or one month, for example. The information processing server 1 also obtains, from the estimation result DB 12d, the estimated ovulation date within the predetermined period of tame after the measurement date among the estimated ovulation dates associated with the user ID. Also, in a case where the latest estimated next menstrual date associated with the user ID falls within the predetermined period of time after the measurement date, the information processing server 1 obtains the latest estimated next menstrual date from the estimation result DB 12d. The information processing server 1 transmits the obtained body temperature value, menstrual date, and ovulation date to the user terminal 2, and the measurement date identifying unit 271 receives these pieces of information. The measurement date identifying unit 271 stores the obtained body temperature value, menstrual date, and ovulation date into the RAM 27c.

The display control unit 273 then determines the reference value of the day before the measurement date to be the default value (step S3).

Based on the obtained menstrual date and ovulation date, the period identifying unit 272 estimates a low-temperature period, a high-temperature period, a first transitional period, and a second transitional period (step S4). For example, the period identifying unit 272 estimates that the first transitional period starts three days before the ovulation date and ends three days after the ovulation date. The period identifying unit 272 also estimates that the second transitional period starts three days before the menstrual date and ends three days after the menstrual date. The period identifying unit 272 also estimates that the low-temperature period starts on the day after the second transitional period and ends on the day before the first transitional period. The period identifying unit 272 also estimates that the high-temperature period starts on the day after the first transitional period and ends on the day before the second transitional period. It should be noted that the sequence of execution of steps S1 to S4. Is not limited to the sequence shown in FIG. 9.

Next, the period identifying unit 272 determines whether the measurement date is included in the first transitional period or the second transitional period (step S5). If the period identifying unit 272 determines that the measurement date is included in the first transitional period or the second transitional period (step S5: YES), the process proceeds to step S6 If the period identifying unit 272 determines that the measurement date is not included in either of the first transitional period and the second transitional period. (step S5: NO), the process proceeds to step S9.

In step S6, the display control unit 273 sets the number of candidates for the input value at 11. The display control unit 273 then sets the distance between adjacent candidates at D1 (step S7). The display control unit 273 further sets the size of each candidate at SZ1 (step S8), and the process proceeds to step S12.

In step S9, the display control unit 273 sets the number of candidates for the input value at 7. The display control unit 273 then sets the distance between adjacent candidates at D2 (step S10). The display control unit 273 further sets the size of each candidate at SZ2 (step S11), and the process proceeds to step S12.

In step S12, the display control unit 273 calculates the value of the first candidate among the determined number of candidates, according to the equation shown below.

First candidate=(the value indicated by the numbers in the tens place, the ones place, and the tenth place of the default value)−0.1×(the number of candidates−1)÷2

The display control unit 273 then sets the values of the second to last candidates among the determined number of candidates (step S13). Where the with candidate is referred to as the candidate i, the candidate i is calculated according to the equation shown below.

Candidate $i$=first candidate+0.1×($i$−1)

Next, the display control unit 273 displays the set number of candidates at intervals of the set distance and in the set size in the display area 100 (step S14). In doing so, the display control unit 273 stores the value of each candidate, and the position and the range of each candidate on the screen into the RAM 27$c$. The display control unit 273 also displays the candidate fractional parts and the confirmation button in the display area 100. In doing so, the display control unit 273 stores the value of each candidate fractional part and the position and the range of each candidate fractional part on the screen into the RAM 27$c$.

As shown in FIG. 10, the input value determining unit 274 then sets a selected value to the value indicated by the numbers in the tens place, the ones place, and the tenth place of the default value, and sets a selected value to the value indicated by the number in the hundredth place of the default value (step S21). The input value determining unit 274 then determines whether a user operation on the touch panel 23 has been detected (step S22). If the input value determining unit 274 determines that any operation has not been detected (step S22: NO), the input value determining unit 274 again performs the determination in step S22. If the input value determining unit 274 determines that an operation has been detected (step S22: YES), the process proceeds to step S23.

In step S23, the input value determining unit 274 determines which candidate or which candidate fractional part is selected, based on coordinates input by a user operation on the screen, and the positions and the ranges of the candidates and the candidate fractional parts stored in the RAM 27$c$. If the input value determining unit 274 determines that a candidate or a candidate fractional part is selected (step S23: YES), the process proceeds to step S24. If the input value determining unit 274 determines that neither a candidate nor a candidate fractional part is selected (step S23: NO), the process proceeds to step S25.

In step S24, in a case where a candidate is selected, the input value determining unit 274 sets the selected value indicated by the numbers in the tens place, the ones place, and the tenth place, as the value of the selected candidate. In a case where a candidate fractional part is selected, the input value determining unit 274 sets the selected value indicated by the number in the hundredth place as the value of the selected candidate fractional part. The input value determining unit 274 then causes the process to proceed to step S22.

In step S25, the input value determining unit 274 determines whether the confirmation button is selected, based on coordinates input by a user operation on the screen. If the input value determining unit 274 determines that the confirmation button is not selected (step S25: NO), the process proceeds to step S22. If the input value determining unit 274 determines that the confirmation button is selected (step S25: YES), the process proceeds to step S26. In step S26, the input value determining unit 274 determines the current selected value to be the input value. The input value determining unit 274 then transmits the user ID, the measurement date, and the input value to the information processing server 1, and ends the process shown in FIGS. 9 and 10. The information processing server 1 associates the user ID, the measurement date, and the input value received from the user terminal 2 with one another, and registers the user ID, the measurement date, and the input value in the body temperature DB 12$b$.

As described above, according to this embodiment, the system control unit 27 identifies the measurement date associated with an input value that is an actual value of the body temperature at a point of time and is an input value to be input this time. In a case where the measurement date is included in a transitional period among the transitional periods during which the body temperature changes within a fluctuation range W2 or W4 and the stable body temperature periods during which the body temperature changes within a fluctuation range W1 or W3 that is narrower than the fluctuation range W2 or W4 in a menstrual cycle, the system control unit 27 displays the first number of candidates. In a case where the measurement date is included in the second period, the system control unit 27 displays the second number of candidates, the second number being smaller than the first number. Accordingly, during the stable body temperature periods with the narrower ranges of fluctuation of the body temperature, display of candidates with low probabilities of being selected can be prevented. Consequently, a smaller number of candidates than that during a transitional period are stored into the RAM 27$c$, and the space in the RAM 27$c$ can be saved accordingly.

Also, the system control unit 27 may display the second number candidates at longer intervals than the intervals at which the first number of candidates are displayed. In this case, the user can be prevented from inadvertently selecting a different candidate from the candidate to be selected.

Also, the system control unit 27 may display each of the second number of candidates in a larger size than the size in which each of the first number of candidates is displayed. In this case, the user can easily select a candidate as intended.

Also, the system control unit 27 may display the candidates determined based on the reference value that has been input as a measured value at a point of time on an earlier day than the measurement date associated with an input value. In this case, the probability of the user selecting one of the candidates can be increased.

Also, the system control unit 27 may display the first or second number of candidates including the reference value that has been input as a measured value at a point of time on the day before the measurement date. In this case, the probability of the user selecting one of the candidates can be increased.

Also, the system control unit 27 may determine that the value indicated by at least part of the number indicating the default value is the median value of the first or second number of candidates. In this case, the probability of the user selecting one of the candidates can be further increased.

2. Second Embodiment

2-1. Outline of the Functions of the System Control Unit

Next, a second embodiment is described. The second embodiment is the same as the first embodiment, except for the aspects described below. In this embodiment, in an earlier menstrual cycle than the menstrual cycle including the measurement date, the display control unit 273 determines the reference value to be a body temperature value that has been input as a measured value at a point of time on a day of the same phase as the phase of the measurement date in the menstrual cycle including the measurement date. The display control unit 273 displays the first or second number of candidates including the body temperature value determined to be the reference value. The measurement date and the day of the same phase as the measurement date are probably the same times in the respective menstrual cycles. The changes in the body temperature in the respective menstrual cycles are similar to each other. Accordingly, the difference between the body temperature on the measurement date and the body temperature on a day of the same phase is probably smaller than the difference between the body temperature on the measurement date and the body temperature on a day of a different phase. Thus, the probability of the user selecting one of the candidates displayed on the screen can be increased.

Figure 11:
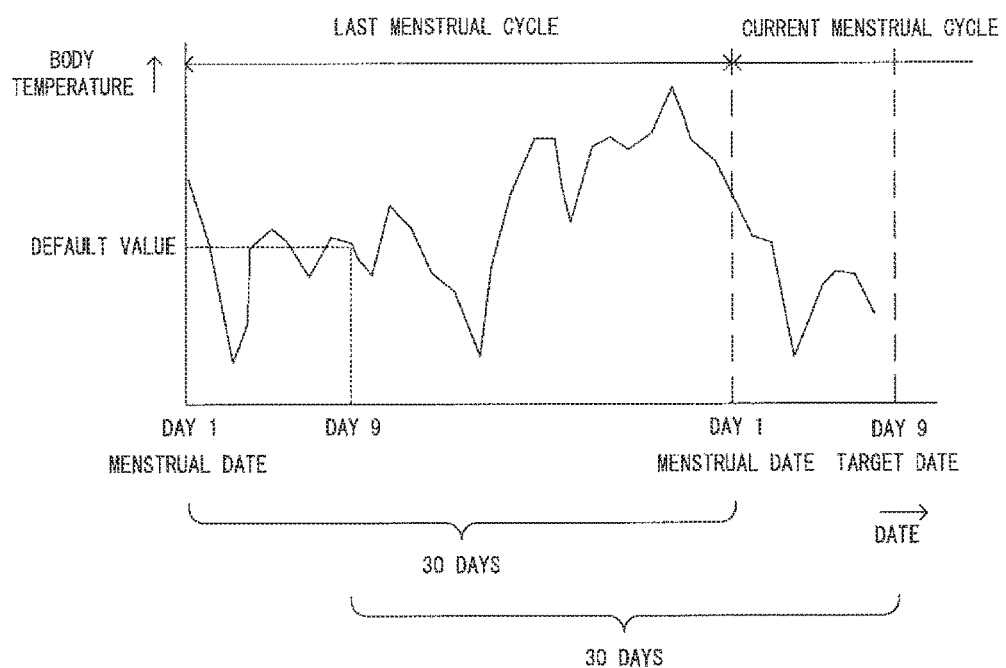
FIG. 11 is a diagram showing an example of a body temperature graph.

FIG. 11 is a diagram showing an example of a body temperature graph. As shown in FIG. 11, the user designates the ninth day in the current menstrual cycle as the measurement date. The number of days in the current menstrual cycle calculated from the next menstrual date estimated by the information processing server 1 is 30, for example. The number of days in the last menstrual cycle is also 30. Accordingly, the day of the same phase as the measurement date in the last menstrual cycle is 30 days before the measurement date. That is, the day of the same phase as the measurement date is the ninth day in the last menstrual cycle. The display control unit 273 may determine the reference value to be the body temperature value measured on this day. Also, the display control unit 273 may identify the day of the same phase as the measurement date in a menstrual cycle that is two or more cycles earlier than the menstrual cycle including the measurement date, for example.

2-2. Operation of the Information Processing System

Figure 12:
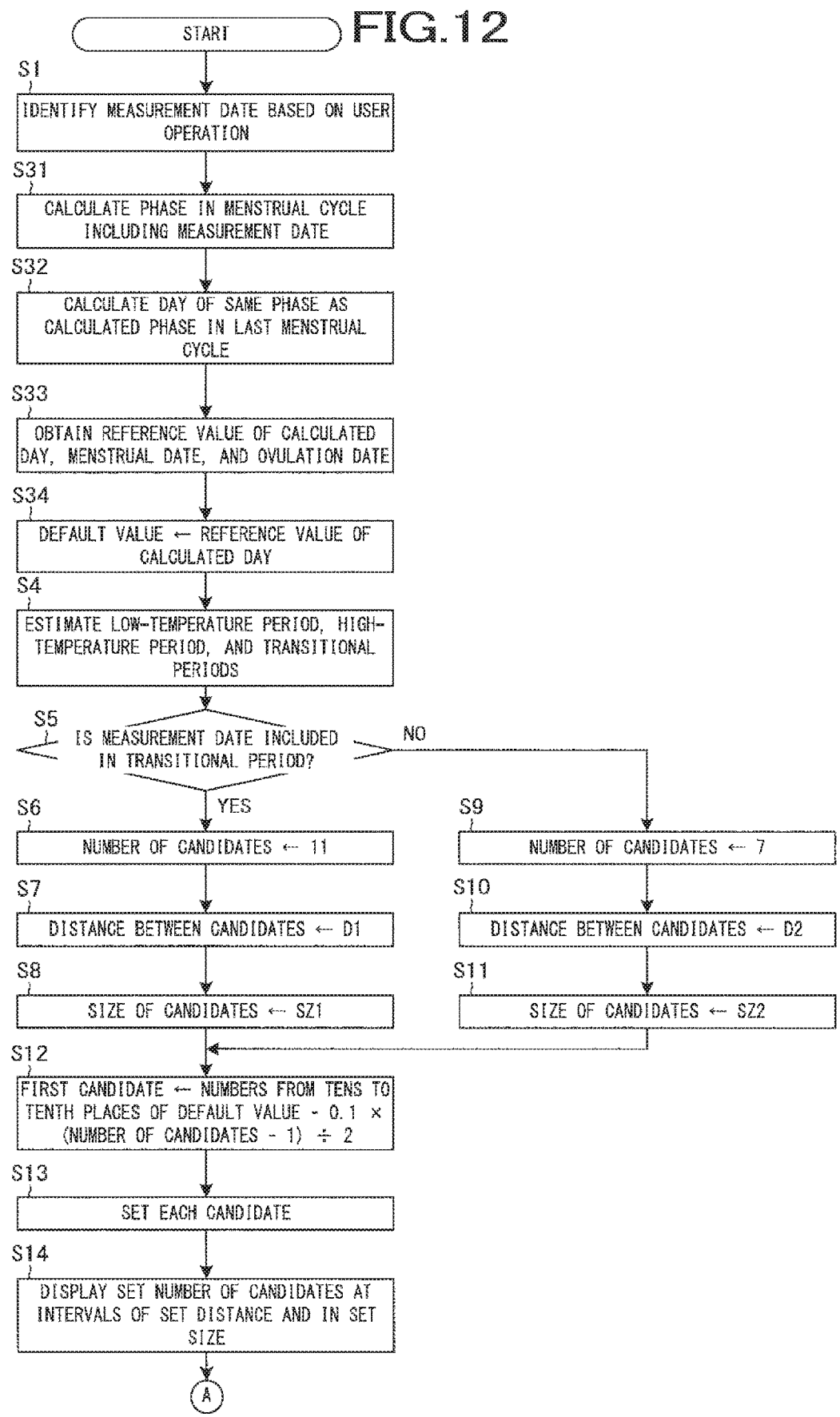
FIG. 12 is a flowchart showing an example of a process to be performed by the system control unit 27 of a user terminal 2 according to an embodiment.

Referring now to FIG. 12, operation of the information processing system S is described. In the case described below, a body temperature value at a point of time on the day of the same phase as the phase of the measurement date in the menstrual cycle including the measurement date is obtained as the reference value, and the reference value is determined to be the default value and the median value of candidates. FIG. 12 is a flowchart showing an example of a process to be performed by the system control unit 27 of a user terminal 2 according to this embodiment. In FIG. 12, the same procedures as those shown in FIG. 9 are denoted by the same reference numerals as those used in FIG. 9. As shown in FIG. 12, step S1 is carried out. The display control unit 273 then calculates the phase of the measurement date in the menstrual cycle including the measurement date (step S31). For example, the display control unit 273 calculates the number of days in the menstrual cycle including the measurement date. The display control unit 273 then calculates the reciprocal of the number of days in the menstrual cycle as a phase per day. The display control unit 273 then calculates the phase of the measurement date by multiplying the number of days between the first day of the menstrual cycle and the measurement date by the phase per day.

The display control unit 273 then calculates the day of the same phase as the calculated phase in an earlier menstrual cycle than the menstrual cycle including the measurement, date (step S32). For example, the display control unit 273 calculates the number of days in the menstrual cycle immediately before the menstrual cycle including the measurement date. The display control unit 273 then calculates the reciprocal of the number of days in the last menstrual cycle as a phase per day. The display control unit. 273 then calculates the number of days by dividing the phase calculated in step S31 by the phase per day in the last menstrual cycle. The display control unit 273 then calculates the day of the same phase by adding the calculated number of cat's to the first day of the last menstrual cycle. In a case where the phase calculated in step S31 is 0, the display control unit 273 determines the first day of the last menstrual cycle to be the day of the same phase.

Next, the measurement date identifying unit 271 obtains the reference value from the information processing server 1. The reference value is the body temperature value on the day calculated in step S32 among the past body temperature values of the user using the user terminal 2. The measurement date identifying unit 271 also obtains a menstrual date and an ovulation date of the user using the user terminal 2, from the information processing server 1 (step S33). For example, the measurement date identifying unit 271 transmits an information request to the information processing server 1. The information request includes the user ID of the user using the user terminal 2, the measurement date, and the date of the calculated day. In the same manner as in step S2 shown in FIG. 9, the information processing server 1 transmits the body temperature value on the calculated day, the menstrual date, and the ovulation date to the user terminal 2, and the measurement date identifying unit 271 receives these pieces of information. The measurement date identifying unit 271 stores the obtained body temperature value, menstrual date, and ovulation date into the RAM 27c. The display control unit 273 then determines the reference value of the day calculated in step S32 to be the default value (step S34).

Steps S4 to S14 and steps S21 to S26 shown in FIG. 10 are then carried out in the same manner as in the first embodiment.

As described above, according to this embodiment, the system control unit 27 displays the first or second number of candidates including the reference value that has been input as a measured value at a point of time on the day of the same phase as the phase of the measurement date in an earlier menstrual cycle than the menstrual cycle including the measurement date. Thus, the probability of the user selecting one of the candidates can be increased.

3. Third Embodiment

3-1. Outline of the Functions of the System Control Unit

Next, a third embodiment is described. The third embodiment is the same as the first or second embodiment, except for the aspects described below. In this embodiment, the display control unit 273 identifies the range of fluctuation of the body temperature during a transitional period and/or the range of fluctuation of the body temperature during a stable body temperature period, based on the past inputs of body temperature values. As for the number of candidates for the input value to be displayed on the screen, the display control unit 273 determines the first number based on the range of fluctuation of the body temperature during a transitional period, or the second number based on the range of fluctuation of the body temperature during a stable body temperature period. In this manner, the number of candidates to be displayed on the screen can be adjusted to a number suitable for the user.

The body temperature DB 12b is also histories of inputs of body temperature values. The display control unit 273 may identify the ranges of fluctuation of the body temperature in the past menstrual cycles, based on the body temperatures registered in the body temperature DB 12b, the menstrual dates registered in the menstrual date DB 12c, and the estimated ovulation dates registered in the estimation result DB 12d. For example, the display control unit 273 identifies each of the past menstrual cycles based on the menstrual dates. Also, the display control unit 273 may identify a low-temperature period, a high-temperature period, a first transitional period, and a second transitional period from each menstrual cycle in the same manner as that described in the first embodiment. The display control unit 273 identifies the range of fluctuation of the body temperature during each of the identified low-temperature period, high-temperature period, first transitional period, and second transitional period. For example, the display control unit 273 identifies the largest value and the smallest value of the body temperature during an identified period. The display control unit 273 determines the difference between the largest value and the smallest value to be the range of fluctuation. The display control unit 273 calculates the representative value of the ranges of fluctuation of the body temperature during the low-temperature periods and the high-temperature periods of all the menstrual cycles. The display control unit 273 also calculates the representative value of the ranges of fluctuation of the body temperature during the first transitional periods and the second transitional periods of all the menstrual cycles. A representative value may be a mean value, a median value, a predetermined percentile, a mode value, or a largest value, for example.

The display control unit 273 may determine the first number based on the representative values of the ranges of fluctuation of the body temperature during the stable body temperature periods. The display control unit 273 may also determine the second number based on the representative values of the ranges of fluctuation of the body temperature during the transitional periods. The representative value of the ranges of fluctuation of the body temperature during the stable body temperature periods is represented by RE1, the representative value of the ranges of fluctuation of the body temperature during the transitional periods is represented by RE2, and the difference between adjacent candidate body temperature values is represented by DF. In this case, the display control unit 273 may calculate the first number and the second number according to the equations shown below.

First number=$INT(RW1 \div DF) \times 2 + 1$

Second number=$INT(RW2 \div DF) \times 2 + 1$

HINT (x) is the function representing the integer portion of x. In this embodiment, DF=0.1. It should be noted that the display control unit 273 may determine the numbers of candidates according to different equations from the above equations. The display control unit 273 may determine the numbers of candidates according to identified ranges of fluctuation. Also, in this embodiment, the display control unit 273 determines odd numbers to be the first number and the second number. However, the display control unit 273 may determine an even number to be at least one of the first and second numbers.

3-2. Operation of the Information Processing System

Figure 13:
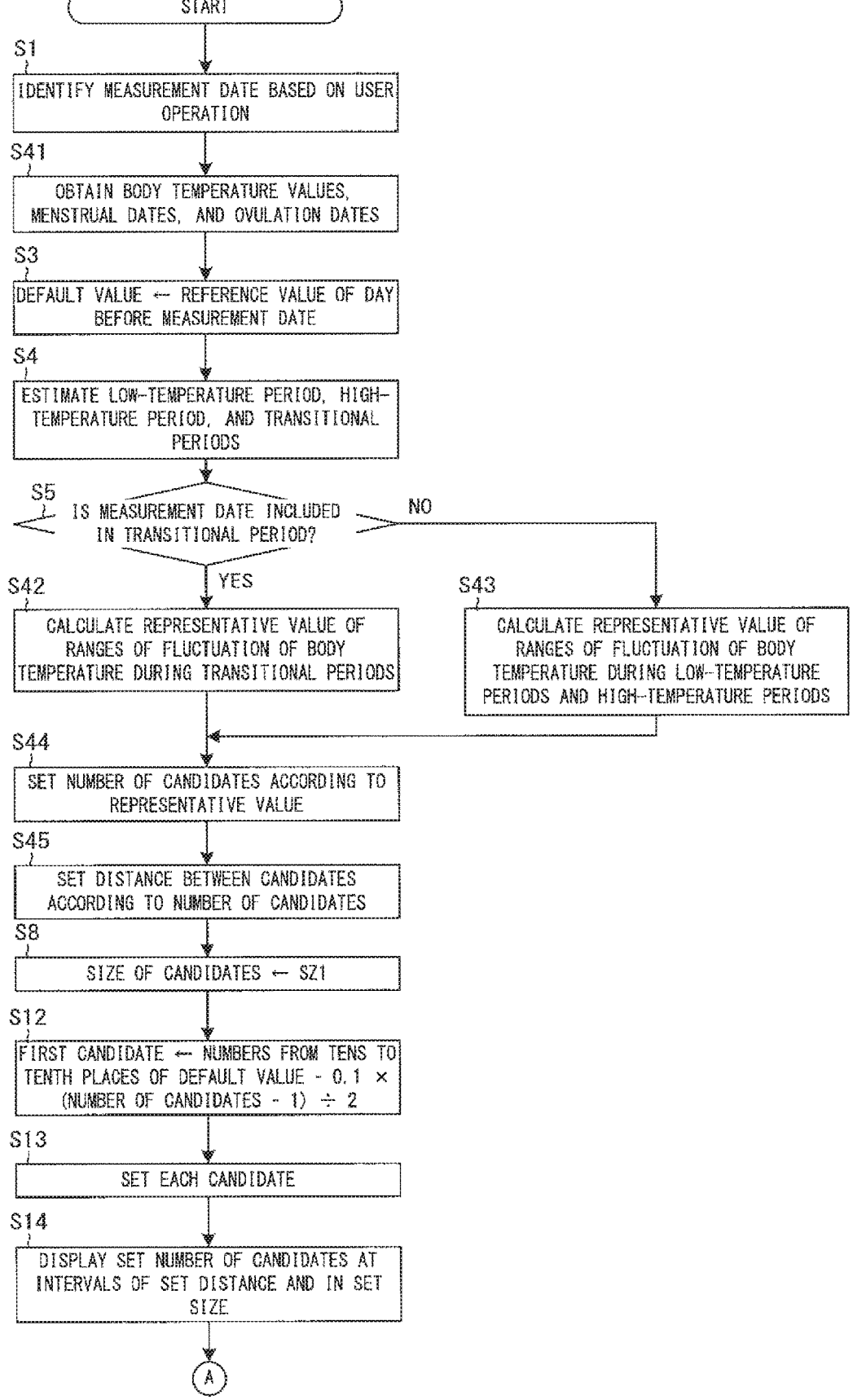
FIG. 13 is a flowchart showing an example of a process to be performed by the system control unit 27 of a user terminal 2 according to an embodiment.

Referring now to FIG. 13, operation of the information processing system S is described. FIG. 13 is a flowchart showing an example of a process to be performed by the system control unit 27 of a user terminal 2 according to this embodiment. In FIG. 13, the same procedures as those shown in FIG. 9 are denoted by the same reference numerals as those used in FIG. 9. As shown in FIG. 13, step S1 is carried out.

The measurement date identifying unit 271 then obtains the past body temperature values, the past menstrual dates, the past ovulation dates of the user using the user terminal 2, from the information processing server 1 (step S41). For example, the measurement date identifying unit 271 transmits an information request including the user ID of the user using the user terminal 2, to the information processing server 1. The information processing server 1 obtains, from the body temperature DB 12b, the respective body temperature values associated with the user ID included in the information request. The information processing server 1 also obtains, from the menstrual date DB 12c, the respective menstrual dates associated with the user ID included in the information request. The information processing server 1 also obtains, from the estimation result DB 12d, the respective estimated ovulation dates associated with the user ID. The information processing server 1 also obtains, from the estimation result DB 12d, the latest menstrual date among the estimated next menstrual dates associated with the user ID. The information processing server 1 transmits the obtained body temperature values, menstrual dates, and ovulation dates to the user terminal 2, and the measurement date identifying unit 271 receives these pieces of information. The measurement date identifying unit 271 stores the obtained body temperature values, menstrual dates, and ovulation dates into the RAM 27c.

Steps S3 to S5 are then carried out. If the period identifying unit 272 determines in step S5 that the measurement date is included in the first transitional period or the second transitional period (step S5: YES), the process proceeds to step S42. If the period identifying unit 272 determines that the measurement date is not included in either of the first transitional period and the second transitional period (step S5: NO), the process proceeds to step S43.

In step S42, the display control unit 273 calculates the representative value of the ranges of fluctuation of the body temperature during the transitional periods, based on the body temperature values obtained from the information processing server 1 and the first and second transitional periods estimated in step S4. In step S43, the display control unit 273 calculates the representative value of the ranges of fluctuation of the body temperature during the stable body temperature transitional periods, based on the body temperature values obtained from the information processing server 1 and the low-temperature and high-temperature periods estimated in step S4.

After carrying out step S42 or S43, the display control unit 273 sets the number of candidates for the input value based on the calculated representative value (step S44). The display control unit 273 then sets the distance between adjacent candidates based on the set number of candidates (step S45). For example, the display control unit 273 may increase the distance as the number of candidates decreases. The display control unit 273 then sets the size of each candidate at SZ1 (step S8). Steps S12 to S14 and steps S21 to S26 shown in FIG. 10 are then carried out in the same manner as in the first embodiment.

In the example shown in FIG. 13, the distance between candidates is set based on the number of candidates. However, the size of each candidate may be increased as the number of candidates decreases. Also, the system control unit 27 may determine the first number and the second number beforehand based on the past inputs of body temperature values, and store the determined first number and second number into the storage unit. 22. Alternatively, the information processing server 1 may determine the first number and the second number for each user beforehand, based on the past inputs of body temperature values. In this case, a user terminal 2 should obtain the first number and the second number associated with the user using the user terminal 2, from the information processing server 1.

As described above, according to this embodiment, the system control unit 27 determines the first number based on the ranges of fluctuation of the body temperature during the transitional periods, and/or the second number based on the ranges of fluctuation of the body temperature during the stable body temperature periods. The ranges of fluctuation are identified from the history of inputs of measured body temperature values. The system control unit 27 also displays the determined first or second number of candidates. Thus, an appropriate number of candidates for the user who inputs an input value can be displayed.

4. Fourth Embodiment 4-1. Outline of the Functions of the System Control Unit Next, a fourth embodiment is described. The fourth embodiment is the same as the first to third embodiments, except for the aspects described below. In this embodiment, in a case where the identified measurement date is included in an estimated transitional period, the period identifying unit 272 identifies the amount of change in the body temperature during the period from a set number of days earlier than the day before the measurement date to the day before the measurement date. In a case where the amount of change is smaller than a set amount, the period identifying unit 272 estimates that a transition from a transitional period to a stable body temperature period has occurred before the measurement date. Accordingly, the display control unit 273 displays the second number of candidates for the input value on the screen. The period identifying unit 272 estimates that a period with a predetermined length including an ovulation date or a menstrual date is a transitional period. In a case where the amount of change until the day before is smaller than the set amount, however, the body temperature can be considered stable for the set number of days. Therefore, there is a high probability that a transition from a transitional period to a stable body temperature period has already occurred in reality. An appropriate number of candidates can be displayed on the basis of the estimation that a transition from a transitional period to a stable body temperature period has already occurred. The set number of days and the set amount may be set beforehand by the manager of the information processing system S, for example.

Figure 14:
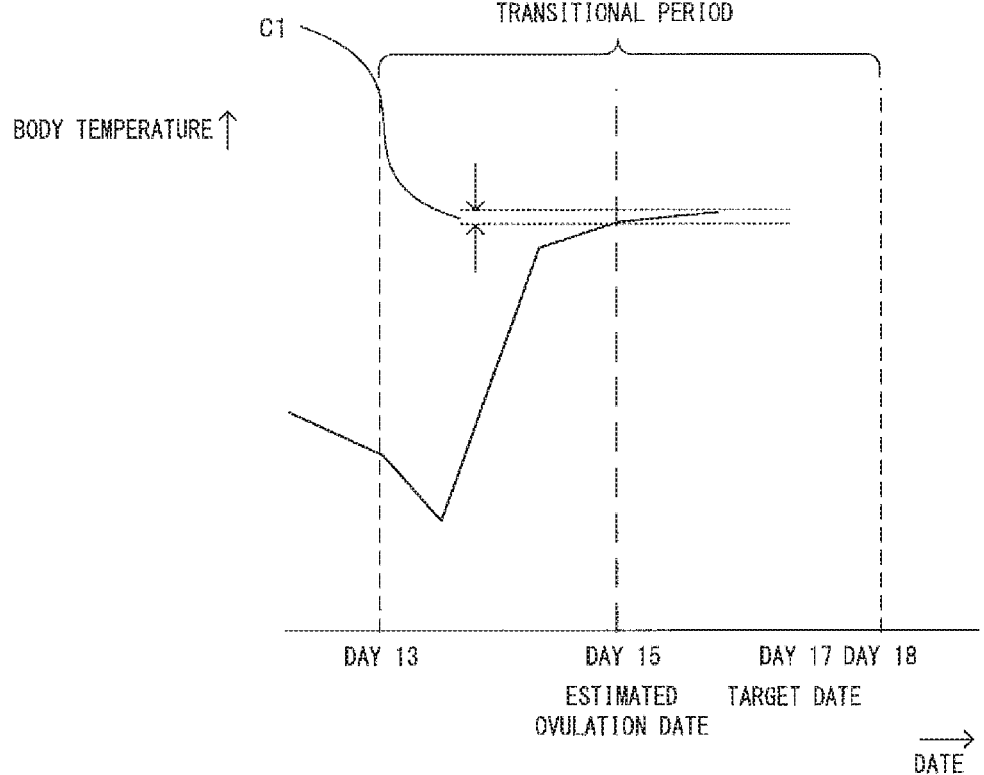
FIG. 14 is a diagram showing an example of a body temperature graph.

FIG. 14 is a diagram showing an example of a body temperature graph. For example, the ovulation date is estimated to be 15 days after the menstrual date. The first transitional period is the period from three days before the ovulation date to three days after the ovulation date. That is, the first transitional period is from the 12th day to the 18th day. The measurement date fails on the 17th day. Accordingly, the measurement date is included in the first transitional period. For example, the set number of days is one. In this case, the display control unit 273 calculates the amount of change as the difference C1 between the body temperature value on the 16th day and the body temperature value on the 15th day. In a case where this amount of change is smaller than the set amount, the display control unit 273 estimates that the 17th day is included in the high-temperature period.

4-2. Operation of the Information Processing System

Figure 15:
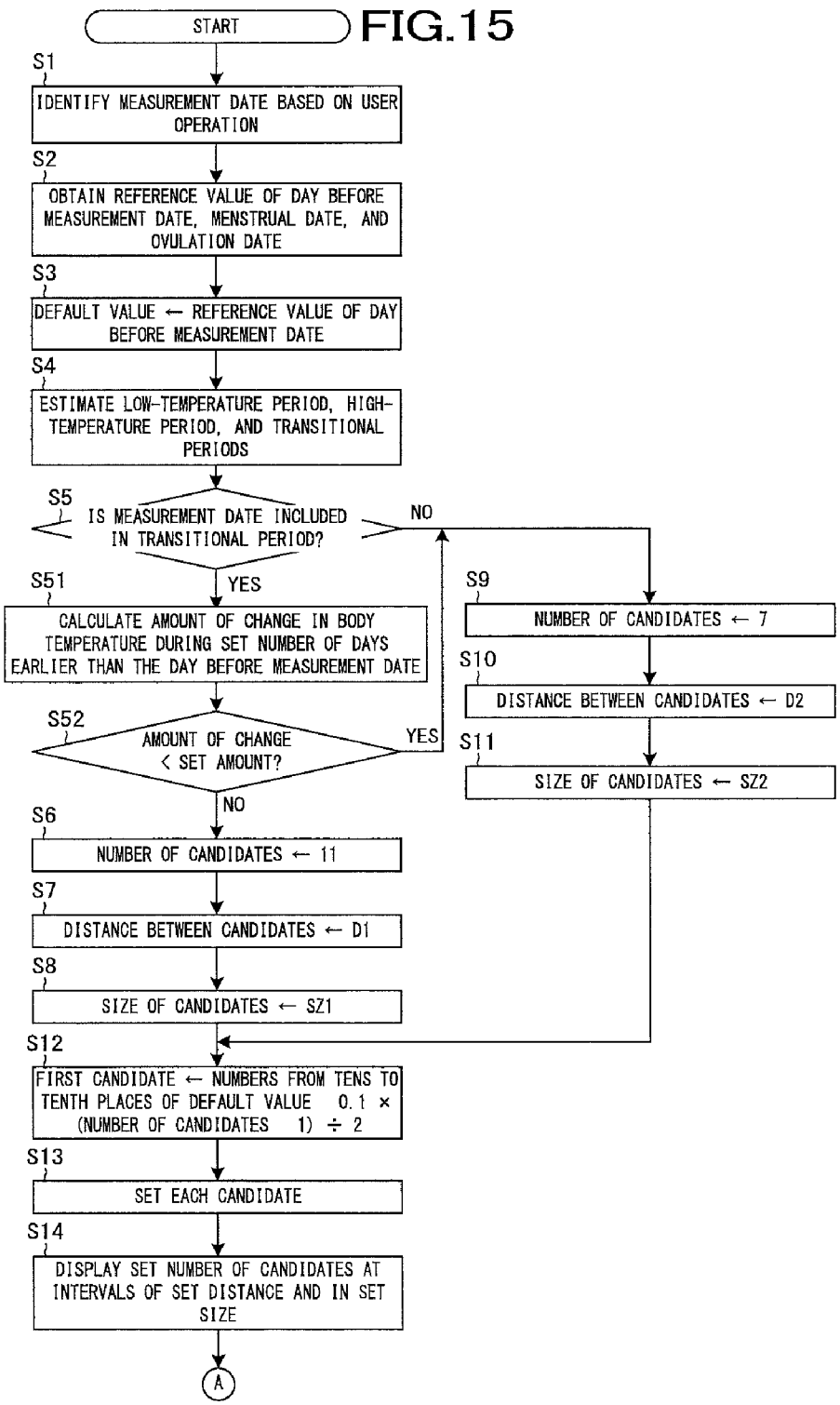
FIG. 15 is a flowchart showing an example of a process to be performed by the system control unit 27 of a user terminal 2 according to an embodiment.

Referring now to FIG. 15, operation of the information processing system S is described. FIG. 15 is a flowchart showing an example of a process to be performed by the system control unit 27 of a user terminal 2 according to this embodiment. In FIG. 15, the same procedures as those shown in FIG. 9 are denoted by the same reference numerals as those used in FIG. 9. As shown in FIG. 15, steps S1 to S5 are carried out. If the period identifying unit 272 determines in step S5 that the measurement date is included in the first transitional period or the second transitional period (step S5: YES), the process proceeds to step S51. If the period identifying unit 272 determines that the measurement date is not included in either of the first transitional period and the second transitional period (step S5: NO), the process proceeds to step S9.

In step S51, the period identifying unit 272 obtains, from the information processing server 1, the body temperature values during the period from the set number of days earlier than the day before the measurement date to the day before the measurement date. For example, the period identifying unit 272 transmits a body temperature request to the information processing server 1. The body temperature request includes the user ID of the user using the user terminal 2, and the dates in the period from the set number of days earlier than the day before the measurement date to the day before the measurement date. The information processing server 1 obtains, from the body temperature DB 12*b*, the body temperature values associated with the respective dates included in the body temperature request among the body temperature values associated with the user ID included in the body temperature request. The information processing server 1 then transmits the obtained body temperature values to the user terminal 2. The period identifying unit 272 calculates the amount of change from the obtained body temperature values. For example, the period identifying unit 272 calculates the difference in body temperature between each two adjacent days. The period identifying unit 272 may then calculate the mean value of the calculated differences in body temperature as the amount of change, for example. The period identifying unit 272 then determines whether the calculated amount of change is smaller than the set value (step S52). If the period identifying unit 272 determines the amount of change not to be smaller than the set value (step S52: NO), steps S6 to S8 are carried out, and the process proceeds to step S12. If the period identifying unit 272 determines the amount of change to be smaller than the set value (step S52: YES), on the other hand, steps S9 to S11 are carried out, and the process proceeds to step S12. Steps S12 to S14 and steps S21 to S26 shown in FIG. 10 are carried out in the same manner as in the first embodiment.

As described above, according to this embodiment, the system control unit 27 estimates a transitional period to be a period with a predetermined length including an ovulation date or a menstrual date. Also, in a case where the identified measurement date is included in an estimated transitional period, the system control unit 27 displays the second number of candidates if the amount of change in the measured value during the period from the predetermined number of days earlier than the day before the measurement date to the day before the measurement date is smaller than the predetermined amount. In this manner, an appropriate number of candidates can be displayed.

5. Modifications

Information to which the present invention can be applied is not limited to body temperature. For example, the present invention can be applied to information that changes in a cyclic manner, and changes in a relatively wide range during a period while changing in a relatively narrow range during another period. Information having such characteristics in some circumstances may be biological information, such as body temperature, blood pressure and pulse, and blood sugar level. However, information to which the present invention can be applied is not limited to biological information.

In each of the above described embodiments, candidates for the input value are divided into a group of candidate values indicated by numbers in the tens place, the ones place, and the tenth place, and a group of candidate values indicated by numbers in the hundredth place. However, the number of groups of candidates may be one, or may be three or more. The number of groups of candidates and the digits corresponding to the respective candidate groups should be determined based on the characteristics of information. The number of candidates in one of the groups of candidates varies with the period including the target date. Such candidates may be values indicated by numbers in digits from the highest-order digit to a predetermined digit.

REFERENCE SIGNS LIST

1 Information processing server
11 Communication unit
12 Storage unit
12a Member DB
12b Body temperature DB
12c Menstrual date DB
12d Estimation result DB
13 Input/output interface
14 System control unit
14a CPU
14b ROM
14c RAM
15 System bus
2 User terminal
21 Communication unit
22 Storage unit
23 Touch panel
23a Display unit
23b Position detecting unit
24 Speaker
25 Microphone
26 Input/output interface
27 System control unit
27a CPU
27b ROM
27c RAM
28 System bus
271 Measurement date identifying unit
272 Period identifying unit
273 Display control unit
274 Input value determining unit
N0 Network
S Information processing system

The invention claimed is:

1. A terminal device comprising:
at least one memory configured to store computer program code; and
at least one processor configured to access said at least one memory and operate according to said computer program code, said computer program code comprising:
identifying code configured to cause at least one of said at least one processor to identify a target date associated with an input value to be input, the input value being related to a value of information at a point of time, the information changing in a cyclic manner; and
control code configured to cause at least one of said at least one processor to display candidates for the input value on a screen, wherein
the control code is configured to cause at least one of said at least one processor to predict a beginning date and an ending date of a current cycle from information relating to a past cycle and/or at least one value obtained in the current cycle, and estimate a reference date that is a predetermined number of days before the predicted ending date of the current cycle,
the control code is configured to cause at least one of said at least one processor to, unless a condition is met, display a first number of candidates based on a determination that the target date is included in a first period, the first period being a period during which the information changes in a first range and estimated with respect to the current cycle based on the reference date,
the control code is configured to cause at least one of said at least one processor to display a second number of candidates based on a determination that the target date is included in a second period, the second period being a period during which the information changes in a second range and estimated with respect to the current cycle based on the reference date, and
the control code is configured to cause at least one of said at least one processor to, in response to the condition being met, display the second number of candidates based on the determination that the target date is included in the first period, wherein the condition is such that an amount of change in the value of the information during a period from a set number of days earlier than a day before the target date to the day before the target date is smaller than a set amount of change,
the second range being narrower than the first range,
the second number being smaller than the first number,
wherein, when the second number of candidates are displayed, the control code is configured to cause at least one of said at least one processor to display such that:
the second number of candidates at longer intervals than intervals at which the first number of candidates are displayed, or
each of the second number of candidates in a larger size than a size of each of the first number of candidates.

2. The terminal device according to claim 1, wherein the control code is configured to cause at least one of said at least one processor to display the candidates determined based on a reference value that has been input as the value of the information at a point of time on an earlier day than the target date.

3. The terminal device according to claim 2, wherein the control code is configured to cause at least one of said at least one processor to display the candidates comprising the reference value.

4. The terminal device according to claim 1, wherein:
the second period comprises a third period during which the value of the information is relatively small, and a fourth period during which the value of the information is relatively large; and
the first period comprises a fifth period during which a transition from the third period to the fourth period occurs, and a sixth period during which a transition from the fourth period to the third period occurs.

5. The terminal device according to claim 1, wherein the computer program code further comprises:
determining code configured to cause at least one of said at least one processor to determine at least one of the first number and the second number, the first number depending on the first range identified based on a history of inputs of values of the information, the second number depending on the second range identified based on the history,
wherein the control code is configured to cause at least one of said at least one processor to display the at least one of the first number and the second number of candidates that is determined.

6. The terminal device according to claim 1, wherein:
the information is body temperature; and
the cycle in which the value of the information changes is a menstrual cycle.

7. The terminal device according to claim 6, wherein the control code is configured to cause at least one of said at least one processor to estimate the first period to be a period with a predetermined length comprising one of an ovulation date and a menstrual date.

8. The terminal device according to claim 1, wherein the first period comprises the reference date.

9. The terminal device according to claim 1, wherein the control code is further configured to cause at least one of said at least one processor to determine the first period as a period that starts a first predetermined number of days before the reference date and ends a second predetermined number of days after the reference date, and determine the second period as a period that starts after the first period ends or a period that ends before the first period starts.

10. The terminal device according to claim 1, wherein the control code is further configured to cause at least one of said at least one processor to determine a reference value, which has been input as the value of the information, as a default value of the information, and determine values of the first number of candidates or values of the second number of candidates for the input value of the information based on a preset function of reference value.

11. The terminal device according to claim 1, wherein the information relating to the past cycle comprise a beginning date and/or an ending date of the past cycle entered by a user.

12. The terminal device according to claim 1, wherein the at least one value obtained in the current cycle comprises body temperatures measured in the past or entered by a user.

13. An information processing method performed by a computer, the method comprising:
identifying a target date associated with an input value to be input, the input value being related to a value of information at a point of time, the information changing in a cyclic manner; and
displaying candidates for the input value on a screen, wherein
the displaying the candidates comprises:
predicting a beginning date and an ending date of a current cycle from information relating to a past cycle and/or at least one value obtained in the current cycle, and estimate a reference date that is a predetermined number of days before the predicted ending date of the current cycle,
unless a condition is met, displaying a first number of candidates based on a determination that the target date is included in a first period, the first period being a period during which the information changes in a first range and estimated with respect to the current cycle based on the reference date,
displaying a second number of candidates based on a determination that the target date is included in a second period, the second period being a period during which the information changes in a second range and estimated with respect to the current cycle based on the reference date, and
in response to the condition being met, displaying the second number of candidates based on the determination that the target date is included in the first period, wherein the condition is such that an amount of change in the value of the information during a period from a set number of days earlier than a day before the target date to the day before the target date is smaller than a set amount of change,
the second range being narrower than the first range,
the second number being smaller than the first number,
wherein the displaying the second number of candidates comprises:
displaying the second number of candidates at longer intervals than intervals at which the first number of candidates are displayed, or
displaying each of the second number of candidates in a larger size than a size of each of the first number of candidates.

14. A non-transitory computer readable medium storing thereon an information processing program, the information processing program, when executed by at least one processor, causing the at least one processor to:
identify a target date associated with an input value to be input, the input value being related to a value of information at a point of time, the information changing in a cyclic manner; and
display candidates for the input value on a screen, by performing:
predicting a beginning date and an ending date of a current cycle from information relating to a past cycle and/or at least one value obtained in the current cycle, and estimate a reference date that is a predetermined number of days before the predicted ending date of the current cycle,
unless a condition is met, displaying a first number of candidates based on a determination that the target date is included in a first period, the first period being a period during which the information changes in a first range and estimated with respect to the current cycle based on the reference date,
displaying a second number of candidates based on a determination that the target date is included in a second period, the second period being a period during which the information changes in a second range and estimated with respect to the current cycle based on the reference date, and in response to the condition being met, displaying the second number of candidates based on the determination that the target date is included in the first period, wherein the condition is such that an amount of change in the value of the information during a period from a set number of days earlier than a day before the target date to the day before the target date is smaller than a set amount of change, the second range being narrower than the first range,
the second number being smaller than the first number,
wherein the displaying the second number of candidates comprises:
- displaying the second number of candidates at longer intervals than intervals at which the first number of candidates are displayed, or
- displaying each of the second number of candidates in a larger size than a size of each of the first number of candidates.

* * * * *